United States Patent
Freitas et al.

(10) Patent No.: US 12,390,775 B1
(45) Date of Patent: Aug. 19, 2025

(54) DEVICES AND METHODS FOR REDUCING THE EFFECTS OF SETTLING OF PARTICLES DURING DROPLET PRODUCTION

(71) Applicant: 10x Genomics, Inc., Pleasanton, CA (US)

(72) Inventors: Daniel Freitas, Oakland, CA (US); Brenden Janatpour Brown, Pleasanton, CA (US); Francis Cui, Oakland, CA (US); Martin Sauzade, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 708 days.

(21) Appl. No.: 17/667,123

(22) Filed: Feb. 8, 2022

Related U.S. Application Data

(60) Provisional application No. 63/146,814, filed on Feb. 8, 2021.

(51) Int. Cl.
    *B01F 33/302* (2022.01)
    *B01F 101/22* (2022.01)

(52) U.S. Cl.
    CPC ...... *B01F 33/3021* (2022.01); *B01F 2101/22* (2022.01); *B01F 2215/0431* (2013.01)

(58) Field of Classification Search
    CPC ..... B01F 33/30; B01F 33/302; B01F 33/3021
    USPC .............................. 366/341, DIG. 1–DIG. 4
    See application file for complete search history.

(56) References Cited

U.S. PATENT DOCUMENTS

| | | | |
|---|---|---|---|
| 6,167,910 B1* | 1/2001 | Chow | B81C 1/00119 137/526 |
| 8,343,443 B2* | 1/2013 | Ying | G01N 35/1095 422/68.1 |
| 9,012,390 B2 | 4/2015 | Holtze et al. | |
| 9,839,911 B2 | 12/2017 | Weitz et al. | |
| 10,011,872 B1 | 7/2018 | Belgrader et al. | |
| 10,323,278 B2 | 6/2019 | Belgrader et al. | |
| 12,005,454 B2 | 6/2024 | Bharadwaj et al. | |
| 2005/0172476 A1 | 8/2005 | Stone et al. | |
| 2006/0163385 A1 | 7/2006 | Link et al. | |
| 2007/0003442 A1 | 1/2007 | Link et al. | |
| 2010/0027372 A1* | 2/2010 | Ozawa | B01F 25/433 137/896 |
| 2014/0155295 A1 | 6/2014 | Hindson et al. | |

(Continued)

FOREIGN PATENT DOCUMENTS

| | | |
|---|---|---|
| WO | WO-2009005680 A1 | 1/2009 |
| WO | WO-2018009766 A1 | 1/2018 |
| WO | WO-2019040637 A1 | 2/2019 |

(Continued)

OTHER PUBLICATIONS

Mazutis et al., "Single-cell analysis and sorting using droplet-based microfluidics," available in PMC Aug. 11, 2014. Published in final edited form as Nat Protoc. 8(5): 870-891 (2013) (48 pages).

(Continued)

*Primary Examiner* — David L Sorkin
(74) *Attorney, Agent, or Firm* — Clark & Elbing LLP

(57) ABSTRACT

Devices, methods, and kits for generating droplets are provided. The devices, methods, and kits are designed to reduce the effects of settling of particles during droplet production.

24 Claims, 5 Drawing Sheets

(56) References Cited

U.S. PATENT DOCUMENTS

2015/0292988 A1 10/2015 Bharadwaj et al.
2019/0060905 A1* 2/2019 Bharadwaj .......... B01F 25/3141

FOREIGN PATENT DOCUMENTS

WO   WO-2019157529 A1   8/2019
WO   WO-2020176882 A1   9/2020

OTHER PUBLICATIONS

Song et al., "Reactions in droplets in microfluidic channels," Angew Chem Int Ed Engl. 45(44):7336-56 (2006).

* cited by examiner

DEVICES AND METHODS FOR REDUCING THE EFFECTS OF SETTLING OF PARTICLES DURING DROPLET PRODUCTION

BACKGROUND OF THE INVENTION

Many biomedical applications rely on high-throughput assays of samples combined with one or more reagents in droplets. For example, in both research and clinical applications, high-throughput genetic tests using target-specific reagents are able to provide information about samples in drug discovery, biomarker discovery, and clinical diagnostics, among others.

Improved devices and methods for producing droplets would be beneficial.

SUMMARY OF THE INVENTION

In one aspect, the invention features a device for producing droplets. The device includes a first channel having a first height, a first width, a first proximal end, and a first distal end; a reservoir having a reservoir height greater than the first height, and an outlet in fluid communication with the first proximal end; a platform having a platform height less than the reservoir height and including a depression on a top surface, wherein the platform is disposed in the reservoir; and a droplet source region in fluid communication with the first distal end.

In some embodiments, the platform height is less than 90% of the reservoir height. In some embodiments, the platform height is between about 300 μm and about 9.9 mm. In some embodiments, the platform height is about 700 μm.

In some embodiments, a side of the platform is slanted. In some embodiments, the side of the platform is at least 93° from horizontal.

In some embodiments, the depression is curved. In some embodiments, the depression has a depth of at least 50 microns.

In some embodiments, the device additionally features a second channel having a second height, a second width, a second proximal end, and a second distal end, wherein the second channel intersects the first channel between the first proximal end and the first distal end. In some embodiments, the droplet source region includes a shelf region having a third height and a third width greater than the first width and being in fluid communication with the first distal end; and a step region including a wall having a fourth height greater than the first and third heights, wherein the shelf region is disposed between the step region and the first distal end.

In one aspect, the invention features a method for producing droplets. The method includes providing a device described herein and flowing a first liquid including particles from the reservoir to the droplet source region via the first channel to produce droplets of the first liquid in a second liquid, wherein particles settle from the first liquid in the reservoir into the depression.

In some embodiments, when the first liquid is depleted from the reservoir, the settled particles remain in the depression. In some embodiments, the method produces droplets including a single particle. In some embodiments, the particles are cells or particulate components thereof.

In some embodiments, the device further includes a second channel having a second height, a second width, a second proximal end, and a second distal end, wherein the second channel intersects the first channel between the first proximal end and the first distal end, and the method further includes flowing a third liquid in the second channel to the intersection to combine the first and third liquids, wherein the droplets include the combined first and third liquids. In some embodiments, the third liquid includes second particles, and the method produces droplets including one of the particles and one of the second particles. In some embodiments, the droplet source region includes a shelf region having a third height and a third width greater than the first width and being in fluid communication with the first distal end; and a step region including a wall having a fourth height greater than the first and third heights, wherein the shelf region is disposed between the step region and the first distal end.

In one aspect, the invention features a device for producing droplets. The device includes a first channel having a first height, a first width, a first proximal end, and a first distal end; a reservoir having a reservoir height greater than the first height and an outlet in fluid communication with the first proximal end, wherein the reservoir includes a slanted wall that reduces the cross-sectional area of the reservoir adjacent to the outlet by between 5-90%; and a droplet source region.

In some embodiments, the slanted wall reduces the cross-sectional area of the reservoir asymmetrically. In some embodiments, the device further includes a second channel having a second height, a second width, a second proximal end, and a second distal end, wherein the second channel intersects the first channel between the first proximal end and the first distal end. In some embodiments, the droplet source region includes a shelf region having a third height and a third width greater than the first width and being in fluid communication with the first distal end; and a step region including a wall having a fourth height greater than the first and third heights, wherein the shelf region is disposed between the step region and the first distal end.

In one aspect, the invention features a method of producing droplets. The method includes providing a device of described above and flowing a first liquid including particles from the reservoir to the droplet source region via the first channel to produce droplets of the first liquid in a second liquid, wherein particles settling from the first liquid in the reservoir flow through the outlet.

In some embodiments, the method produces droplets including a single particle. In some embodiments, the particles are cells or particulate components thereof.

In some embodiments, the device further includes a second channel having a second height, a second width, a second proximal end, and a second distal end, wherein the second channel intersects the first channel between the first proximal end and the first distal end, and the method further includes flowing a third liquid in the second channel to the intersection to combine the first and third liquids, wherein the droplets include the combined first and third liquids. In some embodiments, the third liquid includes second particles, and the method produces droplets including one of the particles and one of the second particles.

In some embodiments, the droplet source region includes a shelf region having a third height and a third width greater than the first width and being in fluid communication with the first distal end; and a step region including a wall having a fourth height greater than the first and third heights, wherein the shelf region is disposed between the step region and the first distal end.

In one aspect, the invention features a kit. The kit includes a device for producing droplets including a first channel having a first height, a first width, a first proximal end, and a first distal end; a reservoir having a reservoir height greater than the first height and an outlet in fluid communication with the first proximal end, wherein the well region is configured to accept an insert; and a droplet source region, and an insert capable of being inserted into the reservoir to reduce the cross-sectional area of the reservoir adjacent to the outlet by between 5-90%.

In some embodiments, the insert is shaped for insertion into reservoir in a manner to asymmetrically reduce the cross-sectional area of the reservoir.

In some embodiments, the device further includes a second channel having a second height, a second width, a second proximal end, and a second distal end, wherein the second channel intersects the first channel between the first proximal end and the first distal end. In some embodiments, the droplet source region includes a shelf region having a third height and a third width greater than the first width and being in fluid communication with the first distal end; and a step region including a wall having a fourth height greater than the first and third heights, wherein the shelf region is disposed between the step region and the first distal end.

In one aspect, the invention features a method of producing droplets. The method includes providing a kit described above; inserting the insert into the reservoir; and flowing a first liquid including particles from the reservoir to the droplet source region via the first channel to produce droplets of the first liquid in a second liquid, wherein particles settling from the first liquid in the reservoir flow through the outlet.

In some embodiments, the method produces droplets including a single particle. In some embodiments, the particles are cells or particulate components thereof.

In some embodiments, the device further includes a second channel having a second height, a second width, a second proximal end, and a second distal end, wherein the second channel intersects the first channel between the first proximal end and the first distal end, and the method further includes flowing a third liquid in the second channel to the intersection to combine the first and third liquids, wherein the droplets include the combined first and third liquids. In some embodiments, the third liquid includes second particles, the method produces droplets including one of the particles and one of the second particles.

In some embodiments, the droplet source region includes a shelf region having a third height and a third width greater than the first width and being in fluid communication with the second distal end; and a step region including a wall having a fourth height greater than the first and third heights, wherein the shelf region is disposed between the step region and the first distal end.

In one aspect, the invention features a device for producing droplets. The device includes a first channel having a first height, a first width, a first proximal end, and a first distal end; a mixing channel having a mixing channel height, width, proximal end, and distal end; a reservoir having a reservoir height greater than the first height and a bottom surface, and being in fluid communication with the first proximal end and the mixing channel distal end; and a droplet source region, wherein the reservoir is fluidically disposed between the mixing channel distal end and the droplet source region.

In some embodiments, the device further includes a secondary reservoir in fluid communication with the mixing channel proximal end.

In one aspect, the invention features a method of producing droplets. The method includes providing a device described above and flowing a secondary liquid into the reservoir via the mixing channel and flowing a first liquid including particles and the secondary liquid from the reservoir to the droplet source region via the first channel to produce droplets of the combined first liquid and secondary liquid in a second liquid, wherein the secondary liquid transports particles that have settled in the reservoir into the first channel.

In some embodiments, the secondary liquid is the same as the first liquid without the particles. In some embodiments, the particles are cells or particulate components thereof. In some embodiments, the device includes a second channel having a second height, a second width, a second proximal end, and a second distal end, wherein the second channel intersects the first channel between the first proximal end and the first distal end, and the method further includes flowing a third liquid in the second channel to the intersection to combine the first, secondary, and third liquids, wherein the droplets include the combined first, secondary, and third liquids. In some embodiments, the third liquid includes second particles, and the method produces droplets including one of the particles and one of the second particles.

In some embodiments, the droplet source region includes a shelf region having a third height and a third width greater than the first width and being in fluid communication with the second distal end; and a step region including a wall having a fourth height greater than the first and third heights, wherein the shelf region is disposed between the step region and the first distal end.

In one aspect, the invention features a method of producing droplets. The method includes providing a device including a mixing channel described herein; flowing a first liquid including particles from the reservoir to the droplet source region via the first channel to produce droplets of the first liquid in a second liquid for a first period of time, wherein particles settle in the reservoir; flowing the first liquid from the reservoir to the mixing channel and from the mixing channel to the reservoir to resuspend settled particles; and flowing the first liquid from the reservoir to the droplet source region via the first channel to produce droplets of the first liquid in a second liquid for a second period of time.

In some embodiments, the particles are cells or particulate components thereof.

In some embodiments, the device further includes a second channel having a second height, a second width, a second proximal end, and a second distal end, wherein the second channel intersects the first channel between the first proximal end and the first distal end, and the method further includes flowing a third liquid in the second channel to the intersection to combine the first and third liquids, wherein the droplets include the combined first and third liquids.

In some embodiments, the third liquid includes second particles, and the method produces droplets including one of the particles and one of the second particles.

In some embodiments, the droplet source region includes a shelf region having a third height and a third width greater than the first width and being in fluid communication with the second distal end; and a step region including a wall having a fourth height greater than the first and third heights, wherein the shelf region is disposed between the step region and the first distal end.

Definitions

To facilitate the understanding of this invention, a number of terms are defined below. Terms defined herein have meanings as commonly understood by a person of ordinary skill in the areas relevant to the invention. Terms such as "a", "an," and "the" are not intended to refer to only a singular entity, but include the general class of which a specific example may be used for illustration. The terminology herein is used to describe specific embodiments of the invention, but their usage does not limit the invention, except as outlined in the claims.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "about," as used herein, refers to ±10% of a recited value.

The terms "adaptor(s)," "adapter(s)," and "tag(s)" may be used synonymously. An adaptor or tag can be coupled to a polynucleotide sequence to be "tagged" by any approach including ligation, hybridization, or other approaches.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "biological particle," as used herein, generally refers to a discrete biological system derived from a biological sample. The biological particle may be a virus. The biological particle may be a cell or derivative of a cell. The biological particle may be an organelle from a cell. Examples of an organelle from a cell include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) including a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell but may not include other constituents of the cell. An example of such constituents is a nucleus or another organelle of a cell. A cell may be a live cell. The live cell may be capable of being cultured, for example, being cultured when enclosed in a gel or polymer matrix or cultured when including a gel or polymer matrix.

The term "flow path," as used herein, refers to a path of channels and other structures for liquid flow from at least one inlet to at least one outlet. A flow path may include branches and may connect to adjacent flow paths, e.g., by a common inlet or a connecting channel.

The term "fluidically connected," as used herein, refers to a direct connection between at least two device elements, e.g., a channel, reservoir, etc., that allows for fluid to move between such device elements without passing through an intervening element.

The term "fluidically disposed between," as used herein, refers to the location of one element between two other elements so that fluid can flow through the three elements in one direction of flow.

The term "genome," as used herein, generally refers to genomic information from a subject, which may be, for example, at least a portion or an entirety of a subject's hereditary information. A genome can be encoded either in DNA or in RNA. A genome can include coding regions that code for proteins as well as non-coding regions. A genome can include the sequence of all chromosomes together in an organism. For example, the human genome has a total of 46 chromosomes. The sequence of all of these together may constitute a human genome.

The term "in fluid communication with", as used herein, refers to a connection between at least two device elements, e.g., a channel, reservoir, etc., that allows for fluid to move between such device elements with or without passing through one or more intervening device elements. When two compartments in fluid communication are directly connected, i.e., connected in a manner allowing fluid exchange without necessity for the fluid to pass through any other intervening compartment, the two compartments are deemed to be fluidically connected.

The term "macromolecular constituent," as used herein, generally refers to a macromolecule contained within or from a biological particle. The macromolecular constituent may include a nucleic acid. In some cases, the biological particle may be a macromolecule. The macromolecular constituent may include DNA or a DNA molecule. The macromolecular constituent may include RNA or an RNA molecule. The RNA may be coding or non-coding. The RNA may be messenger RNA (mRNA), ribosomal RNA (rRNA) or transfer RNA (tRNA), for example. The RNA may be a transcript. The RNA molecule may be (i) a clustered regularly interspaced short palindromic (CRISPR) RNA molecule (crRNA) or (ii) a single guide RNA (sgRNA) molecule. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may include a protein. The macromolecular constituent may include a peptide. The macromolecular constituent may include a polypeptide or a protein. The polypeptide or protein may be an extracellular or an intracellular polypeptide or protein. The macromolecular constituent may also include a metabolite. These and other suitable macromolecular constituents (also referred to as analytes) will be appreciated by those skilled in the art (see U.S. Pat. Nos.

10,011,872 and 10,323,278, and PCT Publication No. WO 2019/157529, each of which is incorporated herein by reference in its entirety).

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may include a nucleotide sequence. The molecular tag may include an oligonucleotide or polypeptide sequence. The molecular tag may include a DNA aptamer. The molecular tag may be or include a primer. The molecular tag may be or include a protein. The molecular tag may include a polypeptide. The molecular tag may be a barcode.

The term "oil," as used herein, generally refers to a liquid that is not miscible with water. An oil may have a density higher or lower than water and/or a viscosity higher or lower than water.

The term "particulate component of a cell" refers to a discrete biological system derived from a cell or fragment thereof and having at least one dimension of 0.1 µm (e.g., at least 0.1 µm, at least 1 µm, at least 10 µm, or at least 100 µm). A particulate component of a cell may be, for example, an organelle, such as a nucleus, endoplasmic reticulum, a ribosome, a Golgi apparatus, an endoplasmic reticulum, a chloroplast, an endocytic vesicle, an exocytic vesicle, a vacuole, a lysosome or a mitochondrion.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a liquid sample, such as a blood sample, urine sample, or saliva sample. The sample may be a skin sample. The sample may be a cheek swab. The sample may be a plasma or serum sample. The sample may include a biological particle, e.g., a cell or virus, or a population thereof, or it may alternatively be free of biological particles. A cell-free sample may include polynucleotides. Polynucleotides may be isolated from a bodily sample that may be selected from the group consisting of blood, plasma, serum, urine, saliva, mucosal excretions, sputum, stool, and tears.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by ILLUMINA®, Pacific Biosciences (PACBIO®), Oxford NANOPORE®, or Life Technologies (ION TORRENT®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "settling," as used herein, refers to a process by which particles, and in particular biological particles, which are otherwise suspended in a liquid, deposit onto a surface over time.

The term "side-channel," as used herein, refers to a channel in fluid communication with, but not fluidically connected to, a droplet source region.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "substantially stationary", as used herein with respect to droplet formation, generally refers to a state when motion of formed droplets in the continuous phase is passive, e.g., resulting from the difference in density between the dispersed phase and the continuous phase.

The term "support," as used herein, generally refers to a particle that is not a biological particle. The particle may be a solid or semi-solid particle. The particle may be a bead, such as a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

BRIEF DESCRIPTION OF THE DRAWINGS

FIGS. 2A and 2B show side (FIG. 2A) and top (FIG. 2B) views of the reservoir design. FIG. 2C shows a perspective view of an exemplary platform design.

FIG. 3A shows the side view of the reservoir with a reduction in the bottom surface area. FIGS. 3B and 3C show top views of the reservoir with (FIG. 3B) and without (FIG. 3C) the reduction in the bottom surface area.

FIG. 4A shows a schematic of the reservoir with the first channel and mixing channel fluidically connected to the base of the reservoir such that the reservoir is fluidically disposed between the first channel and the mixing channel. FIG. 4B shows a schematic of the function of this reservoir design in reducing sedimentation of biological particles in the reservoir. The reservoir and first channel contain a first liquid, which contains cells. During operation of the device, cells settle to the bottom of the reservoir, represented by the black dots. Flowing of a secondary liquid that does not contain cells into the reservoir resuspends the cells that have settled onto the bottom surface of the reservoir back into the mixture of first liquid and secondary liquid, reducing sedimentation of biological particles.

FIG. 5A shows a schematic of the reservoir with the first channel and mixing channel fluidically connected to the base of the reservoir such that the reservoir is fluidically disposed between the first channel and the mixing channel. FIG. 5B shows a schematic of the function of this reservoir design in reducing sedimentation of biological particles in the reservoir. The reservoir and first channel contain a first liquid, which contains cells. During operation of the device, cells settle to the bottom of the reservoir, represented by the black dots. By alternating flow of the first liquid from the reservoir into the mixing channel and from the mixing channel back into the reservoir, the sedimented cells can be resuspended back into the first liquid.

DETAILED DESCRIPTION OF THE INVENTION

Figure 1:
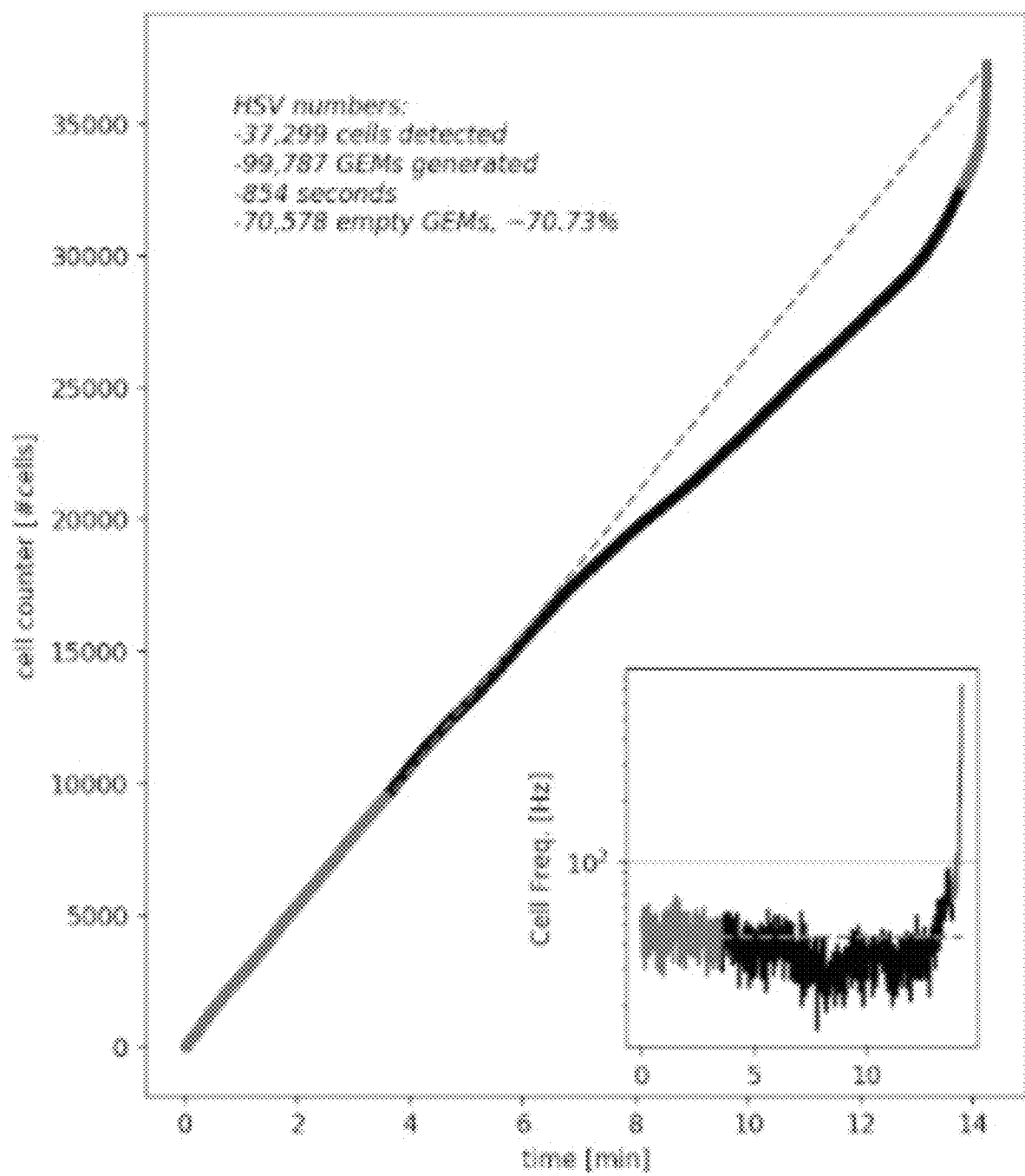
FIG. 1 shows the total number of cells detected in the droplets produced by the device during operation over time. As cells settle onto the bottom surface of the reservoir, there is a drop in the rate of cells detected (#cells/unit time). This rate then increases near the end of device operation, as sedimented cells are drawn from the reservoir and incorporated into droplets. This influx of cells near the end result in an increase in the number of droplets that contain more than one cell. Inset of FIG. 1 shows frequency of cells detected (cells per second) in the droplets produced by the device during operation over time.

The invention provides devices (e.g., microfluidic devices), systems, and methods for forming droplets and methods of their use. FIG. 1 shows the number of cells detected in droplets produced as a function of time during operation of a microfluidic device to form droplets containing cells, and the inset of FIG. 1 shows the frequency of cell detection as a function of time. During operation of device, particles, such as cells, settle to the bottom surface of their holding reservoir, resulting in a reduction in the number of particles, e.g., cells, that are incorporated into the droplets being produced. As the liquid in the reservoir nears depletion, particles, e.g., cells, that have settled onto the bottom surface are drawn into a first channel fluidically connected to the reservoir, resulting in an influx of particles, e.g., cells, and increasing the rate at which particles, e.g., cells, are incorporated into the droplets being produced. In one example, this process results in droplets that contain more than one cell, which cannot be used for further single cell analyses. The invention provides alternative devices, systems, and methods to reduce the number of cells that settle to the bottom of the reservoir during operation of the microfluidic device and thereby increase the number of desired droplets.

Droplet Devices

In general, droplets are provided by a droplet source. The droplets may be first formed by flowing a first liquid through a channel and into a droplet source region including a second liquid, i.e., the continuous phase, which may or may not be actively flowing. Droplets may be formed by any suitable method known in the art. In general, droplet formation includes two liquid phases. The two phases may be, for example, the sample phase and an oil phase. During formation, a plurality of discrete volume droplets is formed.

The droplets may be formed by shaking or stirring a liquid to form individual droplets, creating a suspension or an emulsion containing individual droplets, or forming the droplets through pipetting techniques, e.g., with needles, or the like. The droplets may be formed made using a milli-, micro-, or nanofluidic droplet maker. Examples of such droplet makers include, e.g., a T-junction droplet maker, a Y-junction droplet maker, a channel-within-a-channel junction droplet maker, a cross (or "X") junction droplet maker, a flow-focusing junction droplet maker, a micro-capillary droplet maker (e.g., co-flow or flow-focus), and a three-dimensional droplet maker. The droplets may be produced using a flow-focusing device, or with emulsification systems, such as homogenization, membrane emulsification, shear cell emulsification, and fluidic emulsification.

Discrete liquid droplets may be encapsulated by a carrier fluid that wets the microchannel. These droplets, sometimes known as plugs, form the dispersed phase in which the reactions occur. Systems that use plugs differ from segmented-flow injection analysis in that reagents in plugs do not come into contact with the microchannel. In T junctions, the disperse phase and the continuous phase are injected from two branches of the "T". Droplets of the disperse phase are produced as a result of the shear force and interfacial tension at the fluid-fluid interface. The phase that has lower interfacial tension with the channel wall is the continuous phase. To generate droplets in a flow-focusing configuration, the continuous phase is injected through two outside channels and the disperse phase is injected through a central channel into a narrow orifice. Other geometric designs to create droplets would be known to one of skill in the art. Methods of producing droplets are disclosed in Song et al. Angew. Chem. 45:7336-7356, 2006, Mazutis et al. Nat. Protoc. 8 (5): 870-891, 2013, U.S. Pat. No. 9,839,911; U.S. Pub. Nos. 2005/0172476, 2006/0163385, and 2007/0003442, PCT Pub. Nos. WO 2009/005680 and WO 2018/009766. In some cases, electric fields or acoustic waves may be used to produce droplets, e.g., as described in PCT Pub. No. WO 2018/009766.

In one embodiment, the droplet source region includes a shelf region that allows liquid to expand substantially in one dimension, e.g., perpendicular to the direction of flow. The width of the shelf region is greater than the width of the first channel at its distal end. In certain embodiments, the first channel is a channel distinct from a shelf region, e.g., the shelf region widens or widens at a steeper slope or curvature than the distal end of the first channel. In other embodiments, the first channel and shelf region are merged into a continuous flow path, e.g., one that widens linearly or non-linearly from its proximal end to its distal end; in these embodiments, the distal end of the first channel can be considered to be an arbitrary point along the merged first channel and shelf region. In another embodiment, the droplet source region includes a step region, which provides a spatial displacement and allows the liquid to expand in more than one dimension. The spatial displacement may be upward or downward or both relative to the channel. The choice of direction may be made based on the relative density of the dispersed and continuous phases, with an upward step employed when the dispersed phase is less dense than the continuous phase and a downward step employed when the dispersed phase is denser than the continuous phase. Droplet source regions may also include combinations of a shelf and a step region, e.g., with the shelf region disposed between the channel and the step region. Exemplary devices of this embodiment are described in WO 2019/040637 and WO 2020/176882, the droplet forming devices of which are hereby incorporated by reference.

Without wishing to be bound by theory, droplets of a first liquid can be formed in a second liquid by flow of the first liquid from the distal end into the droplet source region. In embodiments with a shelf region and a step region, the stream of first liquid expands laterally into a disk-like shape in the shelf region. As the stream of first liquid continues to flow across the shelf region, the stream passes into the step region wherein the droplet assumes a more spherical shape and eventually detaches from the liquid stream. Droplet formation by this mechanism can occur without externally driving the continuous phase, unlike in other systems. It will be understood that the continuous phase may be externally driven during droplet formation, e.g., by gently stirring or vibration but such motion is not necessary for droplet formation.

In these embodiments, the size of the generated droplets is significantly less sensitive to changes in liquid properties. For example, the size of the generated droplets is less sensitive to the dispersed phase flow rate. Adding multiple source regions is also significantly easier from a layout and manufacturing standpoint. The addition of further source regions allows for formation of droplets even in the event that one droplet source region becomes blocked. Droplet formation can be controlled by adjusting one or more geometric features of fluidic channel architecture, such as a width, height, and/or expansion angle of one or more fluidic channels. For example, droplet size and speed of droplet formation may be controlled. In some instances, the number of regions of formation at a driven pressure can be increased to increase the throughput of droplet formation.

Passive flow of the continuous phase may occur simply around the nascent droplet. The droplet source region may also include one or more channels that allow for flow of the continuous phase to a location between the distal end of the first channel and the bulk of the nascent droplet. These channels allow for the continuous phase to flow behind a nascent droplet, which modifies (e.g., increase or decreases) the rate of droplet formation. Such channels may be fluidically connected to a reservoir of the droplet source region or to different reservoirs of the continuous phase. Although externally driving the continuous phase is not necessary, external driving may be employed, e.g., to pump continuous phase into the droplet source region via additional channels. Such additional channels may be to one or both lateral sides of the nascent droplet or above or below the plane of the nascent droplet.

In general, the components of a device provided by the methods of the invention, e.g., channels, may have certain geometric features that at least partly determine the sizes of the droplets. For example, any of the channels described herein have a depth, a height, $h_0$, and width, w. The droplet source region may have an expansion angle, $\alpha$. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

As a non-limiting example, for a channel with w=21 µm, h=21 µm, and $\alpha$=3°, the predicted droplet size is 121 µm. In another example, for a channel with w=25 µm, h=25 µm, and $\alpha$=5°, the predicted droplet size is 123 µm. In yet another example, for a channel with w=28 µm, h=28 µm, and $\alpha$=7°, the predicted droplet size is 124 µm. In some instances, the expansion angle may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

The depth and width of the first channel may be the same, or one may be larger than the other, e.g., the width is larger than the depth, or first depth is larger than the width. In some embodiments, the depth and/or width is between about 0.1 µm and 1000 µm. In some embodiments, the depth and/or width of the first channel is from 1 to 750 µm, 1 to 500 µm, 1 to 250 µm, 1 to 100 µm, 1 to 50 µm, or 3 to 40 µm. In some cases, when the width and length differ, the ratio of the width to depth is, e.g., from 0.1 to 10, e.g., 0.5 to 2 or greater than 3, such as 3 to 10, 3 to 7, or 3 to 5. The width and depths of the first channel may or may not be constant over its length. In particular, the width may increase or decrease adjacent the distal end. In general, channels may be of any suitable cross section, such as a rectangular, triangular, or circular, or a combination thereof. In particular embodiments, a channel may include a groove along the bottom surface. The width or depth of the channel may also increase or decrease, e.g., in discrete portions, to alter the rate of flow of liquid or particles or the alignment of particles.

Devices may also include additional channels that intersect the first channel between its proximal and distal ends, e.g., one or more second channels having a second depth, a second width, a second proximal end, and a second distal end. Each of the first proximal end and second proximal ends are or are configured to be in fluid communication with, e.g., fluidically connected to, a source of liquid, e.g., a reservoir integral to the device or coupled to the device, e.g., by tubing. The inclusion of one or more intersection channels allows for splitting liquid from the first channel or introduction of liquids into the first channel, e.g., that combine with the liquid in the first channel or do not combine with the liquid in the first channel, e.g., to form a sheath flow. Channels can intersect the first channel at any suitable angle, e.g., between 5° and 135° relative to the centerline of the first channel, such as between 75° and 115° or 85° and 95°. Additional channels may similarly be present to allow introduction of further liquids or additional flows of the same liquid. Multiple channels can intersect the first channel on the same side or different sides of the first channel. When multiple channels intersect on different sides, the channels may intersect along the length of the first channel to allow liquid introduction at the same point. Alternatively, channels may intersect at different points along the length of the first channel. In some instances, a channel configured to direct a liquid containing a plurality of particles may contain one or more grooves in one or more surface of the channel to direct the plurality of particles towards the droplet formation fluidic connection. For example, such guidance may increase single occupancy rates of the generated droplets. These additional channels may have any of the structural features discussed above for the first channel.

Devices may include multiple first channels, e.g., to increase the rate of droplet formation. In general, throughput may significantly increase by increasing the number of droplet source regions of a device. For example, a device having five droplet source regions may generate five times as many droplets than a device having one droplet source region, provided that the liquid flow rate is substantially the same. A device may have as many droplet source regions as is practical and allowed for the size of the source of liquid, e.g., reservoir. For example, the device may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 2000 or more droplet source regions. Inclusion of multiple droplet source regions may require the inclusion of channels that traverse but do not intersect, e.g., the flow path is in a different plane. Multiple first channel may be in fluid communication with, e.g., fluidically connected to, a separate source reservoir and/or a separate droplet source region. In other embodiments, two or more first channels are in fluid communication with, e.g., fluidically connected to, the same fluid source, e.g., where the multiple first channels branch from a single, upstream channel. The droplet source region may include a plurality of inlets in fluid communication with the first proximal end and a plurality of outlets (e.g., plurality of outlets in fluid communication with a collection region) (e.g., fluidically connected to the first proximal end and in fluid communication with a plurality of outlets). The number of inlets and the number of outlets in the droplet source region may be the same (e.g., there may be 3-10 inlets and/or 3-10 outlets). Alternatively or in addition, the throughput of droplet formation can be increased by increasing the flow rate of the first liquid. In some cases, the throughput of droplet formation can be increased by providing a plurality of single droplet forming devices, e.g., devices with a first channel and a droplet source region, in a single device, e.g., parallel droplet formation.

The width of a shelf region may be from 0.1 μm to 1000 μm. In particular embodiments, the width of the shelf is from 1 to 750 μm, 10 to 500 μm, 10 to 250 μm, or 10 to 150 μm. The width of the shelf region may be constant along its length, e.g., forming a rectangular shape. Alternatively, the width of the shelf region may increase along its length away from the distal end of the first channel. This increase may be linear, nonlinear, or a combination thereof. In certain embodiments, the shelf widens 5% to 10,000%, e.g., at least 300%, (e.g., 10% to 500%, 100% to 750%, 300% to 1000%, or 500% to 1000%) relative to the width of the distal end of the first channel. The depth of the shelf can be the same as or different from the first channel. For example, the bottom of the first channel at its distal end and the bottom of the shelf region may be coplanar. Alternatively, a step or ramp may be present where the distal end meets the shelf region. The depth of the distal end may also be greater than the shelf region, such that the first channel forms a notch in the shelf region. The depth of the shelf may be from 0.1 to 1000 μm, e.g., 1 to 750 μm, 1 to 500 μm, 1 to 250 μm, 1 to 100 μm, 1 to 50 μm, or 3 to 40 μm. In some embodiments, the depth is substantially constant along the length of the shelf. Alternatively, the depth of the shelf slopes, e.g., downward or upward, from the distal end of the liquid channel to the step region. The final depth of the sloped shelf may be, for example, from 5% to 1000% greater than the shortest depth, e.g., 10 to 750%, 10 to 500%, 50 to 500%, 60 to 250%, 70 to 200%, or 100 to 150%. The overall length of the shelf region may be from at least about 0.1 μm to about 1000 μm, e.g., 0.1 to 750 μm, 0.1 to 500 μm, 0.1 to 250 μm, 0.1 to 150 μm, 1 to 150 μm, 10 to 150 μm, 50 to 150 μm, 100 to 150 μm, 10 to 80 μm, or 10 to 50 μm. In certain embodiments, the lateral walls of the shelf region, i.e., those defining the width, may be not parallel to one another. In other embodiments, the walls of the shelf region may narrow from the distal end of the first channel towards the step region. For example, the width of the shelf region adjacent the distal end of the first channel may be sufficiently large to support droplet formation. In other embodiments, the shelf region is not substantially rectangular, e.g., not rectangular or not rectangular with rounded or chamfered corners.

A step region includes a spatial displacement (e.g., depth). Typically, this displacement occurs at an angle of approximately 90°, e.g., between 85° and 95°. Other angles are possible, e.g., 10-90°, e.g., 20 to 90°, 45 to 90°, or 70 to 90°. The spatial displacement of the step region may be any suitable size to be accommodated on a device provided by the methods of the invention, as the ultimate extent of displacement does not affect performance of the device. Preferably the displacement is several times the diameter of the droplet being formed. In certain embodiments, the displacement is from about 1 μm to about 10 cm, e.g., at least 10 μm, at least 40 μm, at least 100 μm, or at least 500 μm, e.g., 40 μm to 600 μm. In some embodiments, the displacement is at least 40 μm, at least 45 μm, at least 50 μm, at least 55 μm, at least 60 μm, at least 65 μm, at least 70 μm, at least 75 μm, at least 80 μm, at least 85 μm, at least 90 μm, at least 95 μm, at least 100 μm, at least 110 μm, at least 120 μm, at least 130 μm, at least 140 μm, at least 150 μm, at least 160 μm, at least 170 μm, at least 180 μm, at least 190 μm, at least 200 μm, at least 220 μm, at least 240 μm, at least 260 μm, at least 280 μm, at least 300 μm, at least 320 μm, at least 340 μm, at least 360 μm, at least 380 μm, at least 400 μm, at least 420 μm, at least 440 μm, at least 460 μm, at least 480 μm, at least 500 μm, at least 520 μm, at least 540 μm, at least 560 μm, at least 580 μm, or at least 600 μm. In some cases, the depth of the step region is substantially constant. Alternatively, the depth of the step region may increase away from the shelf region, e.g., to allow droplets that sink or float to roll away from the spatial displacement as they are formed. The step region may also increase in depth in two dimensions relative to the shelf region, e.g., both above and below the plane of the shelf region. The reservoir may have an inlet and/or an outlet for the addition of continuous phase, flow of continuous phase, or removal of the continuous phase and/or droplets.

While dimension of the devices provided by the methods of the invention may be described as width or depths, the channels, shelf regions, and step regions may be disposed in any plane. For example, the width of the shelf may be in the x-y plane, the x-z plane, the y-z plane or any plane therebetween. In addition, a droplet source region, e.g., including a shelf region, may be laterally spaced in the x-y plane relative to the first channel or located above or below the first channel. Similarly, a droplet source region, e.g., including a step region, may be laterally spaced in the x-y plane, e.g., relative to a shelf region or located above or below a shelf region. The spatial displacement in a step region may be oriented in any plane suitable to allow the nascent droplet to form a spherical shape. The fluidic components may also be in different planes so long as connectivity and other dimensional requirements are met.

A device may also include reservoirs for liquid reagents. For example, the device may include a reservoir for the liquid to flow in the first channel and/or a reservoir for the liquid into which droplets are formed. In some cases, devices include a collection region, e.g., a volume for collecting formed droplets. A collection region may be a reservoir that houses continuous phase or can be any other suitable structure, e.g., a channel, a shelf, or a cavity, on or in the device. For reservoirs or other elements used in collection, the walls may be smooth and not include an orthogonal element that would impede droplet movement. For example, the walls may not include any feature that at least in part protrudes or recedes from the surface. It will be understood, however, that such elements may have a ceiling or floor. The droplets that are formed may be moved out of the path of the next droplet being formed by gravity (either upward or downward depending on the relative density of the droplet and continuous phase). Alternatively or in addition, formed droplets may be moved out of the path of the next droplet being formed by an external force applied to the liquid in the collection region, e.g., gentle stirring, flowing continuous phase, or vibration. Similarly, a reservoir for liquids to flow in additional channels, such as those intersecting the first channel may be present. A single reservoir may also be connected to multiple channels in a device, e.g., when the same liquid is to be introduced at two or more different locations in the device. Waste reservoirs or overflow reservoirs may also be included to collect waste or overflow when droplets are formed. Alternatively, the device may be configured to mate with sources of the liquids, which may be external reservoirs such as vials, tubes, or pouches. Similarly, the device may be configured to mate with a separate component that houses the reservoirs. Reservoirs may be of any appropriate size, e.g., to hold 10 µL to 500 mL, e.g., 10 µL to 300 mL, 25 µL to 10 mL, 100 µL to 1 mL, 40 µL to 300 µL, 1 mL to 10 mL, or 10 mL to 50 mL. When multiple reservoirs are present, each reservoir may have the same or a different size.

Reservoirs may contain a first liquid (optionally a third liquid, or a fourth liquid). The first liquid (or third liquid or fourth liquid) may contain particles, optionally wherein the particles are cells or cell components. If the reservoir contains a liquid which contains particles, settling may occur.

In a non-limiting example, a reservoir may contain a raised platform. The platform may be between about 300 µm and about 9.9 mm (e.g., between about 300 µm and about 5 mm, between about 300 µm and about 2 mm, between about 300 µm and about 1 mm, between about 400 µm and about 900 µm, between about 500 µm and about 900 µm, between about 600 µm and about 800 µm, or between about 650 µm and about 750 µm; about 600 µm, about 650 µm, about 700 µm, about 750 µm, or about 800 µm) in height. The platform may contain a depression on the top surface, e.g., to retain settled cells as liquid is removed. The depression on the top surface of the platform may be curved. The depression may have a depth of about 50 µm (about 20 µm, about 30 µm, about 40 µm, about 45 µm, about 50 µm, about 55 µm, about 60 µm, about 70 µm, about 80 µm). The height of the platform may be between 1% and 90% (e.g., between 1% and 75%, between 1% and 50%, between 1% and 25%, between 1% and 10%, between 1% and 5%, between 5% and 50%, between 5% and 25%, between 5% and 15%, between 5% and 10%, between 10% and 50%, between 10% and 25%, about 80%, about 60%, about 40%, about 25%, about 20%, about 18%, about 16%, about 15%, about 14%, about 13%, about 12%, about 11%, about 10%, about 9%, about 7%, about 5%) of the height of the reservoir. The sides of the platform may be sloped. In certain embodiments, the angle of the sloped sides of the platform is between 90° and 140° (e.g., between 90° and 130°, between 90° and 120°, between 90° and 100°, between 95° and 100°, between 100° and 120°, between 120° and 140°, between 95° and 115°, between 100° and 130°, about 95°, about 96°, about 97°, about 98°, about 99°, about 100°, about 110°, about 120°, about 130°, about) 140° from the horizontal. In certain embodiments, the platform may be molded together with the reservoir, while in other embodiments, the platform may be a separate object inserted into the reservoir. The depression on the top surface of the platform may be used to trap a fraction of particles (e.g., trap between 5% and 90% of particles, trap between 5% and 80% of particles, trap between 5% and 50% of particles, trap between 5% and 25% of particles, trap between 10% and 100% of particles, trap between 10% and 80% of particles, trap between 20% and 100% of particles, trap between 20% and 80% of particles, trap between 40% and 100% of particles, trap between 60% and 100% of particles, trap between 60% and 80% of particles, trap between 50% and 70% of particles, trap between 50% and 90% of particles, trap between 50% and 100% of particles, trap between 25% and 75% of particles, trap between 30% and 70% of particles, trap about 40% of particles, trap about 50% of particles, trap about 60% of particles, trap about 70% of particles, trap about 80% of particles, trap about 90% of particles, trap about 100% of particles) that would otherwise settle onto the bottom surface of the reservoir.

Reservoirs may be designed to have a reduced surface area of the bottom surface of the reservoir to reduce sedimentation of particles. In a non-limiting example, the reservoirs may be shaped to reduced surface area on the bottom surface. The reduction of the bottom surface area or cross-sectional area adjacent to the outlet may be between 5% and 90% (e.g., between 25% and 90%, between 50% and 90%, between 75% and 90%, between 80% and 90%, between 85% and 90%, between 25% and 75%, between 25% and 50%, between 50% and 90%, between 50% and 75%, between 5% and 50%, between 5% and 75%, about 10%, about 20%, about 30%, about 40%, about 50%, about 60%, about 70%, about 75%, about 80%, about 85%, about 86%, about 87%, about 88%, about 89%, about 90%). The reservoir may be shaped symmetrically (e.g., radially symmetric) or asymmetrically. The shape of the reservoir may be achieved by molding the reservoir with the shape directly or by an insert placed in the reservoir. The reduced surface area reduces the availability of settled particles to be reentrained and incorporated into droplets Reservoirs may also be fluidically connected to one or more channels. In a non-limiting example, a reservoir may be fluidically connected to a first channel and a mixing channel, and in particular, the reservoir may be fluidically disposed between the first channel and the mixing channel. This design may permit the flowing of liquids into and out of the reservoir in a manner that resuspends settled particles.

In addition to the components discussed above, devices can include additional components. For example, channels may include filters to prevent introduction of debris into the device. In some cases, the microfluidic devices provided by the methods described herein may include one or more liquid flow units to direct the flow of one or more liquids, such as the aqueous liquid and/or the second liquid immiscible with the aqueous liquid. In some instances, the liquid flow unit may include a compressor to provide positive pressure at an upstream location to direct the liquid from the upstream location to flow to a downstream location. In some instances, the liquid flow unit may include a pump to provide negative pressure at a downstream location to direct the liquid from an upstream location to flow to the downstream location. In some instances, the liquid flow unit may include both a compressor and a pump, each at different locations. In some instances, the liquid flow unit may include different devices at different locations. The liquid flow unit may include an actuator. In some instances, where the second liquid is substantially stationary, the reservoir may maintain a constant pressure field at or near each droplet source region. Devices may also include various valves to control the flow of liquids along a channel or to allow introduction or removal of liquids or droplets from the device. Suitable valves are known in the art. Valves useful for a device of the present invention include diaphragm valves, solenoid valves, pinch valves, or a combination thereof. Valves can be controlled manually, electrically, magnetically, hydraulically, pneumatically, or by a combination thereof. The device may also include integral liquid pumps or be connectable to a pump to allow for pumping in the first channels and any other channels requiring flow. Examples of pressure pumps include syringe, peristaltic, diaphragm pumps, and sources of vacuum. Other pumps can employ centrifugal or electrokinetic forces. Alternatively, liquid movement may be controlled by gravity, capillarity, or surface treatments. Multiple pumps and mechanisms for liquid movement may be employed in a single device. The device may also include one or more vents to allow pressure equalization, and one or more filters to remove particulates or other undesirable components from a liquid. The device may also include one or more inlets and or outlets, e.g., to introduce liquids and/or remove droplets. Such additional components may be actuated or monitored by one or more controllers or computers operatively coupled to the device, e.g., by being integrated with, physically connected to (mechanically or electrically), or by wired or wireless connection.

In a non-limiting example, the first channel can carry a first fluid (e.g., aqueous) and the second channel can carry a second fluid (e.g., oil) that is immiscible with the first fluid. The two fluids can communicate at a junction. In some instances, the first fluid in the first channel may include suspended particles. The particles may be supports (e.g., beads), biological particles, cells, cell beads, or any combination thereof (e.g., a combination of supports and cells or a combination of supports and cell beads, etc.). A discrete droplet generated may include a particle, such as when one or more particles are suspended in the volume of the first fluid that is propelled into the second fluid. Alternatively, a discrete droplet generated may include more than one particle. Alternatively, a discrete droplet generated may not include any particles. For example, in some instances, a discrete droplet generated may contain one or more biological particles where the first fluid in the first channel includes a plurality of biological particles.

Alternatively or in addition, one or more piezoelectric elements may be used to control droplet formation acoustically.

The piezoelectric element may be operatively coupled to a first end of a buffer substrate (e.g., glass). A second end of the buffer substrate, opposite the first end, may include an acoustic lens. In some instances, the acoustic lens can have a spherical, e.g., hemispherical, cavity. In other instances, the acoustic lens can be a different shape and/or include one or more other objects for focusing acoustic waves. The second end of the buffer substrate and/or the acoustic lens can be in contact with the first fluid in the first channel. Alternatively, the piezoelectric element may be operatively coupled to a part (e.g., wall) of the first channel without an intermediary substrate. The piezoelectric element can be in electrical communication with a controller. The piezoelectric element can be responsive to (e.g., excited by) an electric voltage driven at RF frequency. In some cases, the piezoelectric element can be made from zinc oxide (ZnO).

The frequency that drives the electric voltage applied to the piezoelectric element may be from about 5 to about 300 megahertz (MHz), e.g., about 5 MHz, about 6 MHZ, about 7 MHz, about MHz, about 9 MHz, about 10 MHz, about 20 MHz, about 30 MHZ, about 40 MHz, about 50 MHz, about 60 MHZ, about 70 MHz, about 80 MHZ, about 90 MHz, about 100 MHz, about 110 MHz, about 120 MHZ, about 130 MHZ, about 140 MHz, about 150 MHz, about 160 MHz, about 170 MHz, about 180 MHz, about 190 MHz, about 200 MHz, about 210 MHz, about 220 MHz, about 230 MHz, about 240 MHz, about 250 MHz, about 260 MHz, about 270 MHz, about 280 MHz, about 290 MHz, or about 300 MHz. Alternatively, the RF energy may have a frequency range of less than about 5 MHz or greater than about 300 MHz. As will be appreciated, the necessary voltage and/or the RF frequency driving the electric voltage may change with the properties of the piezoelectric element (e.g., efficiency).

Before an electric voltage is applied to a piezoelectric element, the first fluid and the second fluid may remain separated at or near the junction via an immiscible barrier. When the electric voltage is applied to the piezoelectric element, it can generate acoustic waves (e.g., sound waves) that propagate in the buffer substrate. The buffer substrate, such as glass, can be any material that can transfer acoustic waves. The acoustic lens of the buffer substrate can focus the acoustic waves towards the immiscible interface between the two immiscible fluids. The acoustic lens may be located such that the interface is located at the focal plane of the converging beam of the acoustic waves. Upon impact of the sound burst on the barrier, the pressure of the acoustic waves may cause a volume of the first fluid to be propelled into the second fluid, thereby generating a droplet or particle of the volume of the first fluid in the second fluid. In some instances, each propelling may generate a plurality of droplets or particles (e.g., a volume of the first fluid propelled breaks off as it enters the second fluid to form a plurality of discrete droplets or particles). After ejection of the droplet or particle, the immiscible interface can return to its original state. Subsequent applications of electric voltage to the piezoelectric element can be repeated to subsequently generate more droplets or particles. A plurality of droplets or particles can be collected in the second channel for continued transportation to a different location (e.g., reservoir), direct harvesting, and/or storage. Beneficially, the droplets or particles generated can have substantially uniform size, velocity (when ejected), and/or directionality.

In some cases, a device may include a plurality of piezoelectric elements working independently or cooperatively to achieve the desired formation (e.g., propelling) of droplets or particles. For example, the first channel can be coupled to at least 1, 2, 3, 4, 5, 6, 7, 8, 9, 10, 20, 30, 40, 50, 60, 70, 80, 90, 100, 200, 300, 400, or 500 piezoelectric elements. In an example, multiple piezoelectric elements may be positioned adjacent to one another along an axis parallel of the first channel. Alternatively or in addition, multiple piezoelectric elements may circumscribe the first channel. In some instances, the plurality of piezoelectric elements may each be in electrical communication with the same controller or one or more different controllers. The plurality of piezoelectric elements may each transmit acoustic waves from the same buffer substrate or one or more different buffer substrates. In some instances, a single buffer substrate may include a plurality of acoustic lenses at different locations.

In some instances, the first channel may be in fluid communication with a third channel. The third channel may carry the first fluid to the first channel such as from a reservoir of the first fluid. The third channel may include one or more piezoelectric elements, for example, as described herein. As described elsewhere herein, the third channel may carry first fluid with one or more particles (e.g., supports (e.g., beads), biological particles, etc.) and/or one or more reagents suspended in the fluid. Alternatively or in addition, the device may include one or more other channels communicating with the first channel and/or the second channel.

The number and duration of electric voltage pulses applied to the piezoelectric element may be adjusted to control the speed of droplet or particle generation. For example, the frequency of droplet or particle generation may increase with the number of electric voltage pulses. Additionally, the material and size of the piezoelectric element, material and size of the buffer substrate, material, size, and shape of the acoustic lens, number of piezoelectric elements, number of buffer substrates, number of acoustic lenses, respective locations of the one or more piezoelectric elements, respective locations of the one or more buffer substrates, respective locations of the one or more acoustic lenses, dimensions (e.g., length, width, height, expansion angle) of the respective channels, level of electric voltage applied to the piezoelectric element, hydrodynamic forces of the respective fluids, and other factors may be adjusted to control droplet or particle generation speed and/or size of the droplets or particles generated.

A discrete droplet generated may include a particle, such as when one or more supports (e.g., beads) are suspended in the volume of the first fluid that is propelled into the second fluid. Alternatively, a discrete droplet generated may include more than one particle. Alternatively, a discrete droplet generated may not include any particles. For example, in some instances, a discrete droplet generated may contain one or more biological particles where the first fluid in the first channel further includes a suspension of a plurality of biological particles.

In some cases, the droplets or particles formed using a piezoelectric element may be collected in a collection region that is disposed below the droplet or particle generation point. The collection region may be configured to hold a source of fluid to keep the formed droplets or particles isolated from one another. The collection region used after piezoelectric or acoustic element-assisted droplet or particle formation may contain an oil that is continuously circulated, e.g., using a paddle mixer, conveyor system, or a magnetic stir bar. Alternatively, the collection region may contain one or more reagents for chemical reactions that can provide a coating on the droplets or particles to ensure isolation, e.g., polymerization, e.g., thermal- or photo-initiated polymerization.

Surface Properties

A surface of the device may include a material, coating, or surface texture that determines the physical properties of the device. In particular, the flow of liquids through a device of the invention may be controlled by the device surface properties (e.g., wettability of a liquid-contacting surface). In some cases, a device portion (e.g., a region, channel, or sorter) may have a surface having a wettability suitable for facilitating liquid flow (e.g., in a channel) or assisting droplet formation (e.g., in a channel), e.g., if droplet formation is performed.

Wetting, which is the ability of a liquid to maintain contact with a solid surface, may be measured as a function of a water contact angle. A water contact angle of a material can be measured by any suitable method known in the art, such as the static sessile drop method, pendant drop method, dynamic sessile drop method, dynamic Wilhelmy method, single-fiber Wilhelmy method, single-fiber meniscus method, and Washburn's equation capillary rise method. The wettability of each surface may be suited to producing droplets. A device may include a channel having a surface with a first wettability in fluid communication with (e.g., fluidically connected to) a reservoir having a surface with a second wettability. The wettability of each surface may be suited to producing droplets of a first liquid in a second liquid. In this non-limiting example, the channel carrying the first liquid may have a surface with a first wettability suited for the first liquid wetting the channel surface. For example, when the first liquid is substantially miscible with water (e.g., the first liquid is an aqueous liquid), the surface material or coating may have a water contact angle of about 95° or less (e.g., 90° or less). Additionally, in this non-limiting example, a droplet formation region, e.g., including a shelf, may have a surface with a second wettability so that the first liquid de-wets from it. For example, when the second liquid is substantially immiscible with water (e.g., the second liquid is an oil), the material or coating used may have a water contact angle of about 70° or more (e.g., 90° or more, 95° or more, or 100° or more). Typically, in this non-limiting example, the second wettability will be more hydrophobic than the channel. For example, the water contact angles of the materials or coatings employed in the channel and the droplet formation region will differ by 5° to 150°.

For example, portions of the device carrying aqueous phases (e.g., a channel) may have a surface material or coating that is hydrophilic or more hydrophilic than another region of the device, e.g., include a material or coating having a water contact angle of less than or equal to about 90°, and/or the other region of the device may have a surface material or coating that is hydrophobic or more hydrophobic than the channel, e.g., include a material or coating having a water contact angle of greater than 70° (e.g., greater than 90°, greater than 95°, greater than 100° (e.g., 95°-120° or) 100°-150°. In certain embodiments, a region of the device may include a material or surface coating that reduces or prevents wetting by aqueous phases. The device can be designed to have a single type of material or coating throughout. Alternatively, the device may have separate regions having different materials or coatings.

In addition or in the alternative, portions of the device carrying or contacting oil phases (e.g., a collection region or droplet formation region) may have a surface material or coating that is hydrophobic, fluorophilic, or more hydrophobic or fluorophilic than the portions of the device that contact aqueous phases, e.g., include a material or coating having a water contact angle of greater than or equal to about 90°.

The device can be designed to have a single type of material or coating throughout. Alternatively, the device may have separate regions having different materials or coatings. Surface textures may also be employed to control fluid flow.

The device surface properties may be those of a native surface (i.e., the surface properties of the bulk material used for the device fabrication) or of a surface treatment. Non-limiting examples of surface treatments include, e.g., surface coatings and surface textures. In one approach, the device surface properties are attributable to one or more surface coatings present in a device portion. Hydrophobic coatings may include fluoropolymers (e.g., AQUAPEL® glass treatment), silanes, siloxanes, silicones, or other coatings known in the art. Other coatings include those vapor deposited from a precursor such as henicosyl-1,1,2,2-tetrahydrododecyldimethyltris(dimethylaminosilane); henicosyl-1,1,2,2-tetrahydrododecyltrichlorosilane (C12); heptadecafluoro-1,1,2,2-tetrahydrodecyltrichlorosilane (C10); nonafluoro-1,1,2,2-tetrahydrohexyltris(dimethylamino) silane; 3,3,3,4,4,5,5,6,6-nonafluorohexyltrichlorosilane; tridecafluoro-1,1,2,2-tetrahydrooctyltrichlorosilane (C8); bis(tridecafluoro-1,1,2,2-tetrahydrooctyl)dimethylsiloxymethylchlorosilane; nonafluorohexyltriethoxysilane (C6); dodecyltrichlorosilane (DTS); dimethyldichlorosilane (DDMS); or 10-undecenyl-trichlorosilane (V11); pentafluorophenylpropyltrichlorosilane (C5). Hydrophilic coatings include polymers such as polysaccharides, polyethylene glycol, polyamines, and polycarboxylic acids. Hydrophilic surfaces may also be created by oxygen plasma treatment of certain materials.

A coated surface may be formed by depositing a metal oxide onto a surface of the device. Example metal oxides useful for coating surfaces include, but are not limited to, $Al_2O_3$, $TiO_2$, $SiO_2$, or a combination thereof. Other metal oxides useful for surface modifications are known in the art. The metal oxide can be deposited onto a surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be deposited on a surface by contacting it with trimethylaluminum (TMA) and water.

In another approach, the device surface properties may be attributable to surface texture. For example, a surface may have a nanotexture, e.g., have a surface with nanometer surface features, such as cones or columns, that alters the wettability of the surface. Nanotextured surface may be hydrophilic, hydrophobic, or superhydrophobic, e.g., have a water contact angle greater than 150°. Exemplary superhydrophobic materials include Manganese Oxide Polystyrene ($MnO_2$/PS) nano-composite, Zinc Oxide Polystyrene (ZnO/PS) nano-composite, Precipitated Calcium Carbonate, Carbon nano-tube structures, and a silica nano-coating. Superhydrophobic coatings may also include a low surface energy material (e.g., an inherently hydrophobic material) and a surface roughness (e.g., using laser ablation techniques, plasma etching techniques, or lithographic techniques in which a material is etched through apertures in a patterned mask). Examples of low surface energy materials include fluorocarbon materials, e.g., polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly(chloro-trifluoro-ethylene) (CTFE), and poly(vinylidene fluoride) (PVDF). Other superhydrophobic surfaces are known in the art.

In some cases, the water contact angle of a hydrophilic or more hydrophilic material or coating is less than or equal to about 90°, e.g., less than 80°, 70°, 60°, 50°, 40°, 30°, 20°, or 10°, e.g., 90°, 85°, 80°, 75°,70°, 65°, 60°, 55°, 50°, 45°, 40°, 35°, 30°, 25°, 20°, 15°, 10°, 9°, 8°, 7°, 6°, 5°, 4°, 3°, 2°, 1°, or 0°. In some cases, the water contact angle of a hydrophobic or more hydrophobic material or coating is at least 70°, e.g., at least 80°, at least 85°, at least 90°, at least 95°, or at least 100° (e.g., about 100°, 101°, 102°, 103°, 104°, 105°, 106°, 107°, 108°, 109°, 110°, 115°, 120°, 125°, 130°, 135°, 140°, 145°, or about) 150°.

The difference in water contact angles between that of a hydrophilic or more hydrophilic material or coating and a hydrophobic or more hydrophobic material or coating may be 5° to 150°, e.g., 5° to 80°, 5° to 60°, 5° to 50°, 5° to 40°, 5° to 30°, 5° to 20°, 10° to 75°, 15° to 70°, 20° to 65°, 25° to 60°, 30 to 50°, 35° to 45°, e.g., 5°, 6°, 7°, 8°, 9°, 10°, 15°, 20°, 25°, 30°, 35°, 40°, 45°, 50°, 55°, 60, 65°, 70°, 75°, 80°, 85°, 90°, 95°, 100°, 110°, 120°, 130°, 140°, or 150°.

The above discussion centers on the water contact angle. It will be understood that liquids employed in the devices and methods of the invention may not be water, or even aqueous. Accordingly, the actual contact angle of a liquid on a surface of the device may differ from the water contact angle. Furthermore, the determination of a water contact angle of a material or coating can be made on that material or coating when not incorporated into a device of the invention.

Particles

The invention includes methods having particles. For example, particles configured with analyte moieties (e.g., barcodes, nucleic acids, binding molecules (e.g., proteins, peptides, aptamers, antibodies, or antibody fragments), enzymes, substrates, etc.) can be included in a droplet containing an analyte to modify the analyte and/or analyze the presence or concentration of the analyte. In some embodiments, particles are synthetic particles (e.g., supports, e.g., beads, e.g., gel beads).

For example, a droplet may include one or more analyte moieties, e.g., unique identifiers, such as barcodes. Analyte moieties, e.g., barcodes, may be introduced into droplets previous to, subsequent to, or concurrently with droplet formation. The delivery of the analyte moieties, e.g., barcodes, to a particular droplet allows for the later attribution of the characteristics of an individual sample (e.g., biological particle) to the particular droplet. Analyte moieties, e.g., barcodes, may be delivered, for example on a nucleic acid (e.g., an oligonucleotide), to a droplet via any suitable mechanism. Analyte moieties, e.g., barcoded nucleic acids (e.g., oligonucleotides), can be introduced into a droplet via a particle, such as a microcapsule. In some cases, analyte moieties, e.g., barcoded nucleic acids (e.g., oligonucleotides), can be initially associated with the particle (e.g., microcapsule) and then released upon application of a stimulus which allows the analyte moieties, e.g., nucleic acids (e.g., oligonucleotides), to dissociate or to be released from the particle.

A particle, e.g., a support (e.g., a bead), may be porous, non-porous, hollow (e.g., a microcapsule), solid, semi-solid, semi-fluidic, fluidic, and/or a combination thereof. In some instances, a particle, e.g., a support, may be dissolvable, disruptable, and/or degradable. In some cases, a particle, e.g., a support, may not be degradable. In some cases, the particle, e.g., a support, may be a gel bead. A gel bead may be a hydrogel bead. A gel bead may be formed from molecular precursors, such as a polymeric or monomeric species. A semi-solid particle, e.g., a support, may be a liposomal bead. Solid particles, e.g., supports, may include metals including iron oxide, gold, and silver. In some cases, the particle, e.g., the support, may be a silica bead. In some cases, the particle, e.g., a support, can be rigid. In other cases, the particle, e.g., a support, may be flexible and/or compressible.

A particle, e.g., a support (e.g., a bead), may include natural and/or synthetic materials. For example, a particle, e.g., a support, can include a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Supports may also be formed from materials other than polymers, including lipids, micelles, ceramics, glass-ceramics, material composites, metals, other inorganic materials, and others.

In some instances, the particle, e.g., the support (e.g., the bead), may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can include one or more of an acrylamide or a methacrylamide monomer, oligomer, or polymer. In some cases, the particle, e.g., the support, may include prepolymers, which are oligomers capable of further polymerization. For example, polyurethane beads may be prepared using prepolymers. In some cases, the particle, e.g., the support, may contain individual polymers that may be further polymerized together. In some cases, particles, e.g., supports, may be generated via polymerization of different precursors, such that they include mixed polymers, co-polymers, and/or block co-polymers. In some cases, the particle, e.g., the support, may include covalent or ionic bonds between polymeric precursors (e.g., monomers, oligomers, linear polymers), oligonucleotides, primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a support. In some cases, a cross-linker may form disulfide linkages. In some cases, the chemical cross-linker forming disulfide linkages may be cystamine or a modified cystamine.

Particles, e.g., supports (e.g., beads), may be of uniform size or heterogeneous size. In some cases, the diameter of a particle, e.g., a support, may be at least about 1 micrometer ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or greater. In some cases, a particle, e.g., a support, may have a diameter of less than about 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or less. In some cases, a particle, e.g., a support, may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$. The size of a particle, e.g., a support, e.g., a gel bead, used to produce droplets is typically on the order of a cross section of the first channel (width or depth). In some cases, the gel beads are larger than the width and/or depth of the first channel and/or shelf, e.g., at least 1.5×, 2×, 3×, or 4× larger than the width and/or depth of the first channel and/or shelf.

In certain embodiments, particles, e.g., supports (e.g., beads), can be provided as a population or plurality of particles, e.g., supports, having a relatively monodisperse size distribution. Where it may be desirable to provide relatively consistent amounts of reagents within droplets, maintaining relatively consistent particle, e.g., support, characteristics, such as size, can contribute to the overall consistency. In particular, the particles, e.g., supports, described herein may have size distributions that have a coefficient of variation in their cross-sectional dimensions of less than 50%, less than 40%, less than 30%, less than 20%, and in some cases less than 15%, less than 10%, less than 5%, or less.

Particles may be of any suitable shape. Examples of particle, e.g., support (e.g., bead), shapes include, but are not limited to, spherical, non-spherical, oval, oblong, amorphous, circular, cylindrical, and variations thereof.

A particle, e.g., support (e.g., bead), injected or otherwise introduced into a droplet may include releasably, cleavably, or reversibly attached analyte moieties (e.g., barcodes). A particle, e.g., support, injected or otherwise introduced into a droplet may include activatable analyte moieties (e.g., barcodes). A particle, e.g., support, injected or otherwise introduced into a droplet may be a degradable, disruptable, or dissolvable particle, e.g., dissolvable bead.

Particles, e.g., supports (e.g., beads), within a channel may flow at a substantially regular flow profile (e.g., at a regular flow rate). Such regular flow profiles can permit a droplet, when formed, to include a single particle (e.g., support) and a single cell or other biological particle. Such regular flow profiles may permit the droplets to have dual occupancy (e.g., droplets having at least one support and at least one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. In some embodiments, the droplets have a 1:1 dual occupancy (i.e., droplets having exactly one particle (e.g., support) and exactly one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. Such regular flow profiles and devices that may be used to provide such regular flow profiles are provided, for example, in U.S. Patent Publication No. 2015/0292988, which is entirely incorporated herein by reference.

As discussed above, analyte moieties (e.g., barcodes) can be releasably, cleavably or reversibly attached to the particles, e.g., supports (e.g., beads), such that analyte moieties (e.g., barcodes) can be released or be releasable through cleavage of a linkage between the barcode molecule and the particle, e.g., support, or released through degradation of the particle (e.g., support) itself, allowing the barcodes to be accessed or be accessible by other reagents, or both. Releasable analyte moieties (e.g., barcodes) may sometimes be referred to as activatable analyte moieties (e.g., activatable barcodes), in that they are available for reaction once released. Thus, for example, an activatable analyte moiety (e.g., activatable barcode) may be activated by releasing the analyte moiety (e.g., barcode) from a particle, e.g., support (or other suitable type of droplet described herein). Other activatable configurations are also envisioned in the context of the described methods.

In addition to, or as an alternative to the cleavable linkages between the particles, e.g., supports (e.g., beads), and the associated antigen moieties, such as barcode containing nucleic acids (e.g., oligonucleotides), the particles, e.g., supports may be degradable, disruptable, or dissolvable spontaneously or upon exposure to one or more stimuli (e.g., temperature changes, pH changes, exposure to particular chemical species or phase, exposure to light, reducing agent, etc.). In some cases, a particle, e.g., support, may be dissolvable, such that material components of the particle, e.g., support, are degraded or solubilized when exposed to a particular chemical species or an environmental change, such as a change temperature or a change in pH. In some cases, a gel bead can be degraded or dissolved at elevated temperature and/or in basic conditions. In some cases, a particle, e.g., support, may be thermally degradable such that when the particle, e.g., support, is exposed to an appropriate change in temperature (e.g., heat), the particle, e.g., support, degrades. Degradation or dissolution of a particle (e.g., support) bound to a species (e.g., a nucleic acid, e.g., an oligonucleotide, e.g., barcoded oligonucleotide) may result in release of the species from the particle, e.g., support. As will be appreciated from the above disclosure, the degradation of a particle, e.g., support, may refer to the disassociation of a bound or entrained species from a particle, e.g., support, both with and without structurally degrading the physical particle, e.g., support, itself. For example, entrained species may be released from particles, e.g., supports, through osmotic pressure differences due to, for example, changing chemical environments. By way of example, alteration of particle, e.g., support, pore sizes due to osmotic pressure differences can generally occur without structural degradation of the particle, e.g., support, itself. In some cases, an increase in pore size due to osmotic swelling of a particle, e.g., support or microcapsule (e.g., liposome), can permit the release of entrained species within the particle. In other cases, osmotic shrinking of a particle may cause the particle, e.g., support, to better retain an entrained species due to pore size contraction.

A degradable particle, e.g., support (e.g., bead), may be introduced into a droplet, such as a droplet of an emulsion or a well, such that the particle, e.g., support, degrades within the droplet and any associated species (e.g., nucleic acids, oligonucleotides, or fragments thereof) are released within the droplet when the appropriate stimulus is applied. The free species (e.g., nucleic acid, oligonucleotide, or fragment thereof) may interact with other reagents contained in the droplet. For example, a polyacrylamide bead including cystamine and linked, via a disulfide bond, to a barcode sequence, may be combined with a reducing agent within a droplet of a water-in-oil emulsion. Within the droplet, the reducing agent can break the various disulfide bonds, resulting in particle, e.g., support, degradation and release of the barcode sequence into the aqueous, inner environment of the droplet. In another example, heating of a droplet including a particle-, e.g., support-, bound analyte moiety (e.g., barcode) in basic solution may also result in particle, e.g., support, degradation and release of the attached barcode sequence into the aqueous, inner environment of the droplet.

Any suitable number of analyte moieties (e.g., molecular tag molecules (e.g., primer, barcoded oligonucleotide, etc.)) can be associated with a particle, e.g., support (e.g., bead), such that, upon release from the particle, the analyte moieties (e.g., molecular tag molecules (e.g., primer, barcoded oligonucleotide, etc.)) are present in the droplet at a pre-defined concentration. Such pre-defined concentration may be selected to facilitate certain reactions for generating a sequencing library, e.g., amplification, within the droplet. In some cases, the pre-defined concentration of a primer can be limited by the process of producing oligonucleotide-bearing particles, e.g., supports.

Additional reagents may be included as part of the particles (e.g., analyte moieties) and/or in solution or dispersed in the droplet, for example, to activate, mediate, or otherwise participate in a reaction, e.g., between the analyte and analyte moiety.

Biological Samples

A droplet of the invention may include biological particles (e.g., cells) and/or macromolecular constituents thereof (e.g., components of cells (e.g., intracellular or extracellular proteins, nucleic acids, glycans, or lipids) or products of cells (e.g., secretion products)). An analyte from a biological particle, e.g., component or product thereof, may be considered to be a bioanalyte. In some embodiments, a biological particle, e.g., cell, or product thereof is included in a droplet, e.g., with one or more particles (e.g., supports) having an analyte moiety. A biological particle, e.g., cell, and/or components or products thereof can, in some embodiments, be encased inside a gel, such as via polymerization of a droplet containing the biological particle and precursors capable of being polymerized or gelled.

In the case of encapsulated biological particles (e.g., cells), a biological particle may be included in a droplet that contains lysis reagents in order to release the contents (e.g., contents containing one or more analytes (e.g., bioanalytes)) of the biological particles within the droplet. In such cases, the lysis agents can be contacted with the biological particle suspension concurrently with, or immediately prior to the introduction of the biological particles into the droplet source region, for example, through an additional channel or channels upstream or proximal to a second channel or a third channel that is upstream or proximal to a second droplet source region. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be contained in a droplet with the biological particles (e.g., cells) to cause the release of the biological particles' contents into the droplets. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TRITON® X-100 and TWEEN® 20. In some cases, lysis solutions may include ionic surfactants such as, for example, sarcosyl and sodium dodecyl sulfate (SDS). In some embodiments, lysis solutions are hypotonic, thereby lysing cells by osmotic shock. Electroporation, thermal, acoustic or mechanical cellular disruption may also be used in certain cases, e.g., non-emulsion based droplet formation such as encapsulation of biological particles that may be in addition to or in place of droplet formation, where any pore size of the encapsulate is sufficiently small to retain nucleic acid fragments of a desired size, following cellular disruption.

In addition to the lysis agents, other reagents can also be included in droplets with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., cells), the biological particles may be exposed to an appropriate stimulus to release the biological particles or their contents from a microcapsule within a droplet. For example, in some cases, a chemical stimulus may be included in a droplet along with an encapsulated biological particle to allow for degradation of the encapsulating matrix and release of the cell or its contents into the larger droplet. In some cases, this stimulus may be the same as the stimulus described elsewhere herein for release of analyte moieties (e.g., oligonucleotides) from their respective particle (e.g., support). In alternative cases, this may be a different and non-overlapping stimulus, in order to allow an encapsulated biological particle to be released into a droplet at a different time from the release of analyte moieties (e.g., oligonucleotides) into the same droplet.

Additional reagents may also be included in droplets with the biological particles, such as endonucleases to fragment a biological particle's DNA, DNA polymerase enzymes and dNTPs used to amplify the biological particle's nucleic acid fragments and to attach the barcode molecular tags to the amplified fragments. Other reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may include a hybridization region and a template region. The hybridization region can include any sequence capable of hybridizing to the target. In some cases, as previously described, the hybridization region includes a series of G bases to complement the overhanging C bases at the 3' end of a cDNA molecule. The series of G bases may include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos may include deoxyribonucleic acids; ribonucleic acids; modified nucleic acids including 2-Aminopurine, 2,6-Diaminopurine (2-Amino-dA), inverted dT, 5-Methyl dC, 2'-deoxyinosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective droplets, the macromolecular components (e.g., macromolecular constituents of biological particles, such as RNA, DNA, or proteins) contained therein may be further processed within the droplets.

As described above, the macromolecular components (e.g., bioanalytes) of individual biological particles (e.g., cells) can be provided with unique identifiers (e.g., barcodes) such that upon characterization of those macromolecular components, at which point components from a heterogeneous population of cells may have been mixed and are interspersed or solubilized in a common liquid, any given component (e.g., bioanalyte) may be traced to the biological particle (e.g., cell) from which it was obtained. The ability to attribute characteristics to individual biological particles or groups of biological particles is provided by the assignment of unique identifiers specifically to an individual biological particle or groups of biological particles. Unique identifiers, for example, in the form of nucleic acid barcodes, can be assigned or associated with individual biological particles (e.g., cells) or populations of biological particles (e.g., cells), in order to tag or label the biological particle's macromolecular components (and as a result, its characteristics) with the unique identifiers. These unique identifiers can then be used to attribute the biological particle's components and characteristics to an individual biological particle or group of biological particles. This can be performed by forming droplets including the individual biological particle or groups of biological particles with the unique identifiers (via particles, e.g., supports), as described in the methods herein.

In some cases, the unique identifiers are provided in the form of oligonucleotides that include nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given droplet, the nucleic acid barcode sequences contained therein are the same, but as between different droplets, the oligonucleotides can, and do have differing barcode sequences, or at least represent a large number of different barcode sequences across all of the droplets in a given analysis. In some cases, only one nucleic acid barcode sequence can be associated with a given droplet, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

Analyte moieties (e.g., oligonucleotides) in droplets can also include other functional sequences useful in processing of nucleic acids from biological particles contained in the droplet. These sequences include, for example, targeted or random/universal amplification primer sequences for amplifying the genomic DNA from the individual biological particles within the droplets while attaching the associated barcode sequences, sequencing primers or primer recognition sites, hybridization or probing sequences, e.g., for identification of presence of the sequences or for pulling down barcoded nucleic acids, or any of a number of other potential functional sequences.

Other mechanisms of forming droplets containing oligonucleotides may also be employed, including, e.g., coalescence of two or more droplets, where one droplet contains oligonucleotides, or microdispensing of oligonucleotides into droplets, e.g., droplets within microfluidic systems.

In an example, particles (e.g., supports (e.g., beads)) are provided that each include large numbers of the above described barcoded oligonucleotides releasably attached to the supports, where all of the oligonucleotides attached to a particular support will include the same nucleic acid barcode sequence, but where a large number of diverse barcode sequences are represented across the population of supports used. In some embodiments, hydrogel beads, e.g., supports having polyacrylamide polymer matrices, are used as a solid support and delivery vehicle for the oligonucleotides into the droplets, as they are capable of carrying large numbers of oligonucleotide molecules, and may be configured to release those oligonucleotides upon exposure to a particular stimulus, as described elsewhere herein. In some cases, the population of supports will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each support can be provided with large numbers of oligonucleotide molecules attached. In particular, the number of molecules of oligonucleotides including the barcode sequence on an individual support can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of supports are included in droplets, the resulting population of droplets can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each droplet of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given droplet, either attached to a single or multiple particles, e.g., supports, within the droplet. For example, in some cases, mixed, but known barcode sequences set may provide greater assurance of identification in the subsequent processing, for example, by providing a stronger address or attribution of the barcodes to a given droplet, as a duplicate or independent confirmation of the output from a given droplet.

Oligonucleotides may be releasable from the particles (e.g., supports) upon the application of a particular stimulus. In some cases, the stimulus may be a photo-stimulus, e.g., through cleavage of a photo-labile linkage that releases the oligonucleotides. In other cases, a thermal stimulus may be used, where increase in temperature of the particle, e.g., support, environment will result in cleavage of a linkage or other release of the oligonucleotides form the particles, e.g., supports. In still other cases, a chemical stimulus is used that cleaves a linkage of the oligonucleotides to the supports, or otherwise results in release of the oligonucleotides from the particles, e.g., supports. In one case, such compositions include the polyacrylamide matrices described above for encapsulation of biological particles, and may be degraded for release of the attached oligonucleotides through exposure to a reducing agent, such as dithiothreitol (DTT).

The droplets described herein may contain either one or more biological particles (e.g., cells), either one or more barcode carrying particles, e.g., supports, or both at least a biological particle and at least a barcode carrying particle, e.g., support. In some instances, a droplet may be unoccupied and contain neither biological particles nor barcode-carrying particles, e.g., supports. As noted previously, by controlling the flow characteristics of each of the liquids combining at the droplet source region(s), as well as controlling the geometry of the droplet source region(s), droplet formation can be optimized to achieve a desired occupancy level of particles, e.g., supports, biological particles, or both, within the droplets that are generated.

Kits and Systems

Devices provided by the methods of the invention may be combined with various external components, e.g., pumps, reservoirs, or controllers, reagents, e.g., analyte moieties, liquids, particles (e.g., supports), and/or sample in the form of kits and systems. Additionally, kits may contain inserts made from various materials, including, but not limited to, plastics, metals, or composites thereof. Examples of inserts include, but are not limited to, platform inserts that may contain a depression region and inserts that reduce the bottom surface area adjacent to the outlet of the reservoir. The platform insert may be between about 300 µm and about 9.9 mm (e.g., between about 300 µm and about 5 mm, between about 300 µm and about 2 mm, between about 300 µm and about 1 mm, between about 400 µm and about 900 µm, between about 500 µm and about 900 µm, between about 600 µm and about 800 µm, between about 650 µm and about 750 µm, about 600 µm, about 650 µm, about 700 µm, about 750 µm, about 800 µm) in height. The depression on the top surface of the platform may be curved. The depression may have a depth of about 50 µm (about 20 µm, about 30 µm, about 40 µm, about 45 µm, about 50 µm, about 55 µm, about 60 µm, about 70 µm, about 80 µm). The insert fitted into reservoirs to reduce the bottom surface area or cross-sectional area adjacent to the outlet may reduce the surface area by between 5% and 90% (e.g., between 25% and 90%, between 50% and 90%, between 75% and 90%, between 80% and 90%, between 85% and 90%, between 25% and 75%, between 25% and 50%, between 50% and 90%, between 50% and 75%, between 5% and 50%, between 5% and 75%, about 10%, about 20%, about 30%, about 40%, about 50%, about 60%, about 70%, about 75%, about 80%, about 85%, about 86%, about 87%, about 88%, about 89%, about 90%).

The invention also provided kits of first, second, and optionally third liquids as described herein.

Methods

The methods described herein to generate droplets, e.g., of uniform and predictable content, and with high throughput, may be used to greatly increase the efficiency of single cell applications and/or other applications receiving droplet-based input. Such single cell applications and other applications may often be capable of processing a certain range of droplet sizes. The methods may be employed to generate droplets for use as microscale chemical reactors, where the volumes of the chemical reactants are small (~pLs).

Methods of the invention include the step of allowing one or more liquids to flow from the channels (e.g., the first, second, and optional third channel) to the droplet source region.

The methods disclosed herein may produce emulsions, generally, i.e., droplet of a dispersed phases in a continuous phase. For example, droplets may include a first liquid (and optionally a third liquid, and, further, optionally a fourth liquid), and the other liquid may be a second liquid. The first liquid may be substantially immiscible with the second liquid. In some instances, the first liquid may be an aqueous liquid or may be substantially miscible with water. Droplets produced according to the methods disclosed herein may combine multiple liquids. For example, a droplet may combine a first and third liquids. The first liquid may be substantially miscible with the third liquid. The second liquid may be an oil, as described herein.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

The methods described herein may allow for the production of one or more droplets containing a single particle, e.g., support, and/or single biological particle (e.g., cell) with uniform and predictable droplet content. The methods described herein may allow for the production of one or more droplets containing a single particle, e.g., support, and/or single biological particle (e.g., cell) with uniform and predictable droplet size. The methods may also allow for the production of one or more droplets including a single biological particle (e.g., cell) and more than one particle, e.g., support, one or more droplets including more than one biological particle (e.g., cell) and a single particle, e.g., support, and/or one or more droplets including more than one biological particle (e.g., cell) and more than one particle, e.g., supports. The methods may also allow for increased throughput of droplet formation.

Droplets are in general formed by allowing a first liquid, or a combination of a first liquid with a third liquid and optionally fourth liquid, to flow into a second liquid in a droplet source region, where droplets spontaneously form as described herein. The droplet content uniformity may be controlled using, e.g., funnels (e.g., funnels including hurdles), side channels, and/or mixers.

The droplets may include an aqueous liquid dispersed phase within a non-aqueous continuous phase, such as an oil phase. In some cases, droplet formation may occur in the absence of externally driven movement of the continuous phase, e.g., a second liquid, e.g., an oil. As discussed above, the continuous phase may nonetheless be externally driven, even though it is not required for droplet formation. Emulsion systems for creating stable droplets in non-aqueous (e.g., oil) continuous phases are described in detail in, for example, U.S. Pat. No. 9,012,390, which is entirely incorporated herein by reference for all purposes. Alternatively or in addition, the droplets may include, for example, microvesicles that have an outer barrier surrounding an inner liquid center or core. In some cases, the droplets may include a porous matrix that is capable of entraining and/or retaining materials within its matrix. A variety of different vessels are described in, for example, U.S. Patent Application Publication No. 2014/0155295, which is entirely incorporated herein by reference for all purposes. The droplets can be collected in a substantially stationary volume of liquid, e.g., with the buoyancy of the formed droplets moving them out of the path of nascent droplets (up or down depending on the relative density of the droplets and continuous phase). Alternatively or in addition, the formed droplets can be moved out of the path of nascent droplets actively, e.g., using a gentle flow of the continuous phase, e.g., a liquid stream or gently stirred liquid.

Allocating particles, e.g., supports (e.g., microcapsules carrying barcoded oligonucleotides) or biological particles (e.g., cells) to discrete droplets may generally be accomplished by introducing a flowing stream of particles, e.g., supports, in an aqueous liquid into a flowing stream or non-flowing reservoir of a non-aqueous liquid, such that droplets are generated. In some instances, the occupancy of the resulting droplets (e.g., number of particles, e.g., supports, per droplet) can be controlled by providing the aqueous stream at a certain concentration or frequency of particles, e.g., supports. In some instances, the occupancy of the resulting droplets can also be controlled by adjusting one or more geometric features at the point of droplet formation, such as a width of a fluidic channel carrying the particles, e.g., supports, relative to a diameter of a given particles, e.g., supports.

Where single particle-, e.g., support-, containing droplets are desired, the relative flow rates of the liquids can be selected such that, on average, the droplets contain fewer than one particle, e.g., support, per droplet in order to ensure that those droplets that are occupied are primarily singly occupied. In some embodiments, the relative flow rates of the liquids can be selected such that a majority of droplets are occupied, for example, allowing for only a small percentage of unoccupied droplets. The flows and channel architectures can be controlled as to ensure a desired number of singly occupied droplets, less than a certain level of unoccupied droplets and/or less than a certain level of multiply occupied droplets.

The methods described herein can be operated such that a majority of occupied droplets include no more than one biological particle per occupied droplet. In some cases, the droplet formation process is conducted such that fewer than 25% of the occupied droplets contain more than one biological particle (e.g., multiply occupied droplets), and in many cases, fewer than 20% of the occupied droplets have more than one biological particle. In some cases, fewer than 10% or even fewer than 5% of the occupied droplets include more than one biological particle per droplet.

In some cases, settling of particles in the reservoir may cause formation of droplets containing more than the desired number of particles per occupied droplet, i.e., an increase in the number of droplets formed containing more than one particle of a given type per droplet. The reservoir may be modified in the manner described herein to reduce the number of droplets formed that contain more than the desired number of particles per occupied droplet by between 5% and 100% (e.g., by between 75% and 100%, by between 5% and 90%, by between 5% and 50%, by between 5% and 25%, by between 10% and 100%, by between 10% and 80%, by between 20% and 100%, by between 20% and 80%, by between 40% and 100%, by between 60% and 100%, by between 60% and 80%, by between 50% and 70%, by between 50% and 90%, by between 50% and 100%, by between 25% and 75%, by between 30% and 70%, by about 60%, by about 70%, by about 80%, by about 90%, or by about 100%).

In one non-limiting example, the device may include a reservoir containing a first liquid which contains biological particles (e.g., cells or cell components), wherein the reservoir is fluidically disposed between a first channel and a mixing channel, and wherein the first channel also contains the first liquid containing particles and the mixing channel contains a secondary liquid, which may be substantially the same as the first liquid but does not contain particles. Flowing the secondary liquid from the mixing channel into the reservoir resuspends particles that settle onto the bottom surface of the reservoir by between 5% and 100% (e.g., between 25% and 100%, between 50% and 100%, between 75% and 100%, between 80% and 100%, between 75% and 95%, between 25% and 75%, between 25% and 50%, between 50% and 90%, between 50% and 75%, between 5% and 25%, between 5% and 50%, between 5% and 75%, between 5% and 95%, between 25% and 95%, between 50% and 95%, about 10%, about 20%, about 30%, about 40%, about 50%, about 60%, about 70%, about 75%, about 80%, about 85%, about 90%, about 95%, or about 100%). The secondary liquid can flow continuously or intermittently from the mixing channel into the reservoir during droplet production. Each instance of intermittent flow may last between 1-120 seconds or more (e.g., between 1-90 seconds, between 1-60 seconds, between 1-30 seconds, between 1-15 seconds, between 1-10 seconds, between 5-45 seconds, between 5-30 seconds, between 5-15 seconds, between 10-60 seconds, between 10-45 seconds, between 10-30 seconds, between 10-20 seconds, between 20-60 seconds, between 30-60 seconds, about 1 second, about 5 seconds, about 10 seconds, about 15 seconds, about 20 seconds, about 30 seconds, about 45 seconds, about 60 seconds, or more).

In an alternative non-limiting example, the reservoir is fluidically disposed between a first channel and a mixing channel. As particles settle onto the bottom surface of the reservoir during droplet production, the first liquid can be transported from the reservoir into the mixing channel and from the mixing channel back into the reservoir. This alternating or mixing flow can occur one or more times (e.g., 2 times, 3 times, 4 times, 5 times, 6 times, 7 times, 8 times, 9 times, 10 times, about 15 times, about 20 times, about 25 times, about 30 times, about 35 times, about 40 times, or about 50 times) to resuspend particles from the bottom surface of the reservoir into the first liquid. Alternating flow can be used one or more times (e.g., 2 times, 3 times, 4 times, 5 times, 6 times, 7 times, 8 times, 9 times, 10 times, about 15 times, about 20 times, about 25 times, about 30 times, about 35 times, about 40 times, about 50 times) during droplet production.

It may be desirable to avoid the creation of excessive numbers of empty droplets, for example, from a cost perspective and/or efficiency perspective. However, while this may be accomplished by providing sufficient numbers of particles, e.g., supports, into the droplet source region, the Poisson distribution may expectedly increase the number of droplets that may include multiple biological particles. As such, at most about 95%, 90%, 85%, 80%, 75%, 70%, 65%, 60%, 55%, 50%, 45%, 40%, 35%, 30%, 25%, 20%, 15%, 10%, 5% or less of the generated droplets can be unoccupied. In some cases, the flow of one or more of the particles, or liquids directed into the droplet source region can be conducted using methods of the invention such that, in many cases, no more than about 50% of the generated droplets, no more than about 25% of the generated droplets, or no more than about 10% of the generated droplets are unoccupied. These flows can be controlled so as to present non-Poisson distribution of singly occupied droplets while providing lower levels of unoccupied droplets. The above noted ranges of unoccupied droplets can be achieved while still providing any of the single occupancy rates described above. For example, in many cases, the use of methods described herein creates resulting droplets that have multiple occupancy rates of less than about 25%, less than about 20%, less than about 15%, less than about 10%, and in many cases, less than about 5%, while having unoccupied droplets of less than about 50%, less than about 40%, less than about 30%, less than about 20%, less than about 10%, less than about 5%, or less.

The flow of the first fluid may be such that the droplets contain a single particle, e.g., support. In certain embodiments, the yield of droplets containing a single particle is at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

As will be appreciated, the above-described occupancy rates are also applicable to droplets that include both biological particles (e.g., cells) and supports. The occupied droplets (e.g., at least about 10%, 20%, 30%, 40%, 50%, 60%, 70%, 80%, 90%, 95%, or 99% of the occupied droplets) can include both a support and a biological particle. Particles, e.g., supports, within a channel (e.g., a particle channel) may flow at a substantially regular flow profile (e.g., at a regular flow rate; e.g., the flow profile being controlled by one or more side-channels and/or one or more funnels) to provide a droplet, when formed, with a single particle (e.g., support) and a single cell or other biological particle. Such regular flow profiles may permit the droplets to have a dual occupancy (e.g., droplets having at least one support and at least one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. In some embodiments, the droplets have a 1:1 dual occupancy (i.e., droplets having exactly one particle (e.g., support) and exactly one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. Such regular flow profiles and devices that may be used to provide such regular flow profiles are provided, for example, in U.S. Patent Publication No. 2015/0292988, which is entirely incorporated herein by reference.

In some cases, additional particles may be used to deliver additional reagents to a droplet. In such cases, it may be advantageous to introduce different particles (e.g., supports) into a common channel (e.g., proximal to or upstream from a droplet source region) or droplet formation intersection from different support sources (e.g., containing different associated reagents) through different channel inlets into such common channel or droplet source region. In such cases, the flow and/or frequency of each of the different particle, e.g., support, sources into the channel or fluidic connections may be controlled to provide for the desired ratio of particles, e.g., supports, from each source, while optionally ensuring the desired pairing or combination of such particles, e.g., supports, are formed into a droplet with the desired number of biological particles.

The droplets described herein may include small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. For example, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where the droplets further include particles (e.g., supports or microcapsules), it will be appreciated that the sample liquid volume within the droplets may be less than about 90% of the above described volumes, less than about 80%, less than about 70%, less than about 60%, less than about 50%, less than about 40%, less than about 30%, less than about 20%, or less than about 10% the above described volumes (e.g., of a partitioning liquid), e.g., from 1% to 99%, from 5% to 95%, from 10% to 90%, from 20% to 80%, from 30% to 70%, or from 40% to 60%, e.g., from 1% to 5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95%, or 95% to 100% of the above described volumes.

Any suitable number of droplets can be generated. For example, in a method described herein, a plurality of droplets may be generated that includes at least about 1,000 droplets, at least about 5,000 droplets, at least about 10,000 droplets, at least about 50,000 droplets, at least about 100,000 droplets, at least about 500,000 droplets, at least about 1,000,000 droplets, at least about 5,000,000 droplets at least about 10,000,000 droplets, at least about 50,000,000 droplets, at least about 100,000,000 droplets, at least about 500,000,000 droplets, at least about 1,000,000,000 droplets, or more. Moreover, the plurality of droplets may include both unoccupied droplets (e.g., empty droplets) and occupied droplets.

The fluid to be dispersed into droplets may be transported from a reservoir to the droplet source region. Alternatively, the fluid to be dispersed into droplets is formed in situ by combining two or more fluids in a device provided by the methods of the invention. For example, the fluid to be dispersed may be formed by combining one fluid containing one or more reagents with one or more other fluids containing one or more reagents. In these embodiments, the mixing of the fluid streams may result in a chemical reaction. For example, when a particle is employed, a fluid having reagents that disintegrates the particle may be combined with the particle, e.g., immediately upstream of the droplet generating region. In these embodiments, the particles may be cells, which can be combined with lysing reagents, such as surfactants. When particles, e.g., supports, are employed, the particles, e.g., supports, may be dissolved or chemically degraded, e.g., by a change in pH (acid or base), redox potential (e.g., addition of an oxidizing or reducing agent), enzymatic activity, change in salt or ion concentration, or other mechanism.

The first fluid is transported through the first channel at a flow rate sufficient to produce droplets in the droplet source region. Faster flow rates of the first fluid generally increase the rate of droplet production; however, at a high enough rate, the first fluid will form a jet, which may not break up into droplets. Typically, the flow rate of the first fluid though the first channel may be between about 0.01 µL/min to about 100 µL/min, e.g., 0.1 to 50 µL/min, 0.1 to 10 µL/min, or 1 to 5 µL/min. In some instances, the flow rate of the first liquid may be between about 0.04 µL/min and about 40 µL/min. In some instances, the flow rate of the first liquid may be between about 0.01 µL/min and about 100 µL/min. Alternatively, the flow rate of the first liquid may be less than about 0.01 µL/min. Alternatively, the flow rate of the first liquid may be greater than about 40 µL/min, e.g., 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 µL/min, the droplet radius may not be dependent on the flow rate of first liquid. Alternatively or in addition, for any of the abovementioned flow rates, the droplet radius may be independent of the flow rate of the first liquid.

The typical droplet formation rate for a single channel in a device provided by the methods of the invention is between 0.1 Hz to 10,000 Hz, e.g., 1 to 1000 Hz or 1 to 500 Hz. The use of multiple first channels can increase the rate of droplet formation by increasing the number of locations of formation.

As discussed above, droplet formation may occur in the absence of externally driven movement of the continuous phase. In such embodiments, the continuous phase flows in response to displacement by the advancing stream of the first fluid or other forces. Channels may be present in the droplet source region, e.g., including a shelf region, to allow more rapid transport of the continuous phase around the first fluid. This increase in transport of the continuous phase can increase the rate of droplet formation. Alternatively, the continuous phase may be actively transported. For example, the continuous phase may be actively transported into the droplet source region, e.g., including a shelf region, to increase the rate of droplet formation; continuous phase may be actively transported to form a sheath flow around the first fluid as it exits the distal end; or the continuous phase may be actively transported to move droplets away from the point of formation.

Additional factors that affect the rate of droplet formation include the viscosity of the first fluid and of the continuous phase, where increasing the viscosity of either fluid reduces the rate of droplet formation. In certain embodiments, the viscosity of the continuous phase is between 0.5 to 10 cP. Furthermore, lower interfacial tension results in slower droplet formation. In certain embodiments, the interfacial tension is between 0.1 and 100 mN/m (e.g., 1 to 100 mN/m or 2 to 60 mN/m). The depth of the shelf region can also be used to control the rate of droplet formation, with a shallower depth resulting in a faster rate of formation.

The methods may be used to produce droplets in range of 1 to 500 µm in diameter, e.g., 1 to 250 µm, 5 to 200 µm, 5 to 150 µm, or 12 to 125 µm. Factors that affect the size of the droplets include the rate of formation, the cross-sectional dimension of the distal end of the first channel, the depth of the shelf, and fluid properties and dynamic effects, such as the interfacial tension, viscosity, and flow rate.

The first liquid may be aqueous, and the second liquid may be an oil (or vice versa). Examples of oils include perfluorinated oils, mineral oil, and silicone oils. For example, a fluorinated oil may include a fluorosurfactant for stabilizing the resulting droplets, for example, inhibiting subsequent coalescence of the resulting droplets. Examples of particularly useful liquids and fluorosurfactants are described, for example, in U.S. Pat. No. 9,012,390, which is entirely incorporated herein by reference for all purposes. Specific examples include hydrofluoroethers, such as HFE 7500, 7300, 7200, or 7100. Suitable liquids are those described in US 2015/0224466 and U.S. 62/522,292, the liquids of which are hereby incorporated by reference. In some cases, liquids include additional components such as a particle, e.g., a cell or a gel support. As discussed above, the first fluid or continuous phase may include reagents for carrying out various reactions, such as nucleic acid amplification, lysis, or support (e.g., bead) dissolution. The first liquid or continuous phase may include additional components that stabilize or otherwise affect the droplets or a component inside the droplet. Such additional components include surfactants, antioxidants, preservatives, buffering agents, antibiotic agents, salts, chaotropic agents, enzymes, nanoparticles, and sugars.

Methods of the invention may be used for various applications, such as, for example, processing a single analyte (e.g., bioanalytes, e.g., RNA, DNA, or protein) or multiple analytes (e.g., bioanalytes, e.g., DNA and RNA, DNA and protein, RNA and protein, or RNA, DNA and protein) from a single cell. For example, a biological particle (e.g., a cell or virus) can be formed in a droplet, and one or more analytes (e.g., bioanalytes) from the biological particle (e.g., cell) can be modified (e.g., bound, labeled, or otherwise modified by an analyte moiety) for subsequent processing. The multiple analytes may be from the single cell. This process may enable, for example, proteomic, transcriptomic, and/or genomic analysis of the cell or population thereof (e.g., simultaneous proteomic, transcriptomic, and/or genomic analysis of the cell or population thereof).

Methods of modifying analytes include providing a plurality of particles (e.g., supports) in a liquid carrier (e.g., an aqueous carrier); providing a sample containing an analyte (e.g., as part of a cell, or component or product thereof) in a sample liquid; and using a device provided by the methods of the invention to combine the liquids and form an analyte droplet containing one or more particles and one or more analytes (e.g., as part of one or more cells, or components or products thereof). Such sequestration of one or more particles with analyte (e.g., bioanalyte associated with a cell) in a droplet enables labeling of discrete portions of large, heterologous samples (e.g., single cells within a heterologous population). Once labeled or otherwise modified, droplets can be combined (e.g., by breaking an emulsion), and the resulting liquid can be analyzed to determine a variety of properties associated with each of numerous single cells.

In particular embodiments, the invention features methods of producing analyte droplets using a device provided by the methods having a particle channel (e.g., a first channel) and a sample channel (e.g., a second channel or a first side-channel that intersects a second channel) that intersect upstream of a droplet source region. Particles having an analyte moiety in a liquid carrier flow proximal-to-distal (e.g., towards the droplet source region) through the particle channel (e.g., a first channel) and a sample liquid containing an analyte flows in the proximal-to-distal direction (e.g., towards the droplet source region) through the sample channel (e.g., a second channel or a first side-channel that intersects a second channel) until the two liquids meet and combine at the intersection of the sample channel and the particle channel, upstream (and/or proximal to) the droplet source region. The combination of the liquid carrier with the sample liquid results in an analyte liquid. In some embodiments, the two liquids are miscible (e.g., they both contain solutes in water or aqueous buffer). The two liquids may be mixed in a mixer as described herein. The combination of the two liquids can occur at a controlled relative rate, such that the analyte liquid has a desired volumetric ratio of particle liquid to sample liquid, a desired numeric ratio of particles to cells, or a combination thereof (e.g., one particle per cell per 50 pL). As the analyte liquid flows through the droplet source region into a partitioning liquid (e.g., a liquid which is immiscible with the analyte liquid, such as an oil), analyte droplets form. These analyte droplets may continue to flow through one or more channels. Alternatively or in addition, the analyte droplets may accumulate (e.g., as a substantially stationary population) in a droplet collection region. In some cases, the accumulation of a population of droplets may occur by a gentle flow of a fluid within the droplet collection region, e.g., to move the formed droplets out of the path of the nascent droplets.

Methods useful for analysis may feature any combination of elements described herein. For example, various droplet source regions can be employed in the methods. In some embodiments, analyte droplets are formed at a droplet source region having a shelf region, where the analyte liquid expands in at least one dimension as it passes through the droplet source region. Any shelf region described herein can be useful in the methods of analyte droplet formation provided herein. Additionally or alternatively, the droplet source region may have a step at or distal to an inlet of the droplet source region (e.g., within the droplet source region or distal to the droplet source region). In some embodiments, analyte droplets are formed without externally driven flow of a continuous phase (e.g., by one or more crossing flows of liquid at the droplet source region). Alternatively, analyte droplets are formed in the presence of an externally driven flow of a continuous phase.

A device described by the methods of the invention useful for droplet formation may feature multiple droplet source regions (e.g., in or out of (e.g., as independent, parallel circuits) fluid communication with one another. For example, such a device may have 2-100, 3-50, 4-40, 5-30, 6-24, 8-18, or 9-12, e.g., 2-6, 6-12, 12-18, 18-24, 24-36, 36-48, or 48-96, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more droplet source regions configured to produce analyte droplets).

Source reservoirs can store liquids prior to and during droplet formation. In some embodiments, a device provided by the methods of the invention useful in analyte droplet formation includes one or more particle reservoirs connected proximally to one or more particle channels. Particle suspensions can be stored in particle reservoirs (e.g., a first reservoir) prior to analyte droplet formation. Particle reservoirs can be configured to store particles containing an analyte moiety. For example, particle reservoirs can include, e.g., a coating to prevent adsorption or binding (e.g., specific or non-specific binding) of particles or analyte moieties. Additionally or alternatively, particle reservoirs can be configured to minimize degradation of analyte moieties (e.g., by containing nuclease, e.g., DNAse or RNAse) or the particle matrix itself, accordingly.

Additionally or alternatively, a device includes one or more sample reservoirs connected proximally to one or more sample channels. Samples containing cells and/or other reagents useful in analyte and/or droplet formation can be stored in sample reservoirs prior to analyte droplet formation. Sample reservoirs can be configured to reduce degradation of sample components, e.g., by including nuclease (e.g., DNAse or RNAse).

Methods of the invention may include adding a sample and/or particles to a device provided by the methods, for example, (a) by pipetting a sample liquid, or a component or concentrate thereof, into a sample reservoir (e.g., a second reservoir) and/or (b) by pipetting a liquid carrier (e.g., an aqueous carrier) and/or particles into a particle reservoir (e.g., a first reservoir). In some embodiments, the method involves first adding (e.g., pipetting) the liquid carrier (e.g., an aqueous carrier) and/or particles into the particle reservoir prior to adding (e.g., pipetting) the sample liquid, or a component or concentrate thereof, into the sample reservoir. In some embodiments, the liquid carrier added to the particle reservoir includes lysing reagents. Alternatively, the methods of the invention include adding a liquid (e.g., a fourth liquid) containing lysing reagent(s) to a lysing reagent reservoir (e.g., a third reservoir).

The sample reservoir and/or particle reservoir may be incubated in conditions suitable to preserve or promote activity of their contents until the initiation or commencement of droplet formation.

Formation of bioanalyte droplets, as provided herein, can be used for various applications. In particular, by forming bioanalyte droplets using the methods herein, a user can perform standard downstream processing methods to barcode heterogeneous populations of cells or perform single-cell nucleic acid sequencing.

In methods of barcoding a population of cells, an aqueous sample having a population of cells is combined with bioanalyte particles having a nucleic acid primer sequence and a barcode in an aqueous carrier at an intersection of the sample channel and the particle channel to form a reaction liquid. In some embodiments, the bioanalyte particles are in a liquid carrier including lysing reagents. In some embodiments, the lysing reagents are included in a lysing liquid. The lysing reagent(s) (e.g., in a first liquid) may be combined with a sample liquid (e.g., a third liquid) at a channel intersection (e.g., an intersection between a first channel and a second channel). The combined liquids can be mixed in a mixer disposed downstream of the intersection.

Upon passing through the droplet source region, the reaction liquid meets a partitioning liquid (e.g., a partitioning oil) under droplet-forming conditions to form a plurality of reaction droplets, each reaction droplet having one or more of the particles and one or more cells in the reaction liquid. The reaction droplets are incubated under conditions sufficient to allow for barcoding of the nucleic acid of the cells in the reaction droplets. In some embodiments, the conditions sufficient for barcoding are thermally optimized for nucleic acid replication, transcription, and/or amplification. For example, reaction droplets can be incubated at temperatures configured to enable reverse transcription of RNA produced by a cell in a droplet into DNA, using reverse transcriptase. Additionally or alternatively, reaction droplets may be cycled through a series of temperatures to promote amplification, e.g., as in a polymerase chain reaction (PCR).

Accordingly, in some embodiments, one or more nucleotide amplification reagents (e.g., PCR reagents) are included in the reaction droplets (e.g., primers, nucleotides, and/or polymerase). Any one or more reagents for nucleic acid replication, transcription, and/or amplification can be provided to the reaction droplet by the aqueous sample, the liquid carrier, or both. In some embodiments, one or more of the reagents for nucleic acid replication, transcription, and/or amplification are in the aqueous sample.

Also provided herein are methods of single-cell nucleic acid sequencing, in which a heterologous population of cells can be characterized by their individual gene expression, e.g., relative to other cells of the population. Methods of barcoding cells discussed above and known in the art can be part of the methods of single-cell nucleic acid sequencing provided herein. After barcoding, nucleic acid transcripts that have been barcoded are sequenced, and sequences can be processed, analyzed, and stored according to known methods. In some embodiments, these methods enable the generation of a genome library containing gene expression data for any single cell within a heterologous population.

Alternatively, the ability to sequester a single cell in a reaction droplet provided by methods herein enables bioanalyte for applications beyond genome characterization. For example, a reaction droplet containing a single cell and variety of analyte moieties capable of binding different proteins can allow a single cell to be detectably labeled to provide relative protein expression data. In some embodiments, analyte moieties are antigen-binding molecules (e.g., antibodies or fragments thereof), wherein each antibody clone is detectably labeled (e.g., with a fluorescent marker having a distinct emission wavelength). Binding of antibodies to proteins can occur within the reaction droplet, and cells can be subsequently analyzed for bound antibodies according to known methods to generate a library of protein expression. Other methods known in the art can be employed to characterize cells within heterologous populations using the methods provided herein. In one example, following the formation or droplets, subsequent operations that can be performed can include formation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the droplet). An exemplary use for droplets formed using methods of the invention is in performing nucleic acid amplification, e.g., polymerase chain reaction (PCR), where the reagents necessary to carry out the amplification are contained within the first fluid. In the case where a droplet is a droplet in an emulsion, the emulsion can be broken, and the contents of the droplet pooled for additional operations. Additional reagents that may be included in a droplet along with the barcode bearing support may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of poly-T sequence during sequencing and/or sequence the 5' end of a polynucleotide sequence. The amplification products, for example first amplification products and/or second amplification products, may be subject to sequencing for sequence analysis. In some cases, amplification may be performed using the Partial Hairpin Amplification for Sequencing (PHASE) method.

EXAMPLES

Example 1

Figure 2A:
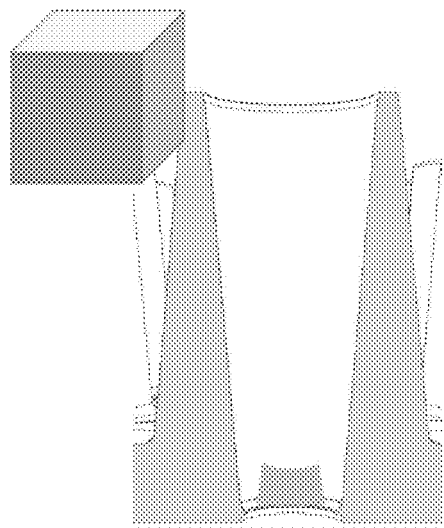
FIGS. 2A-2C show an exemplary design of a reservoir containing a platform.
Figure 2B:
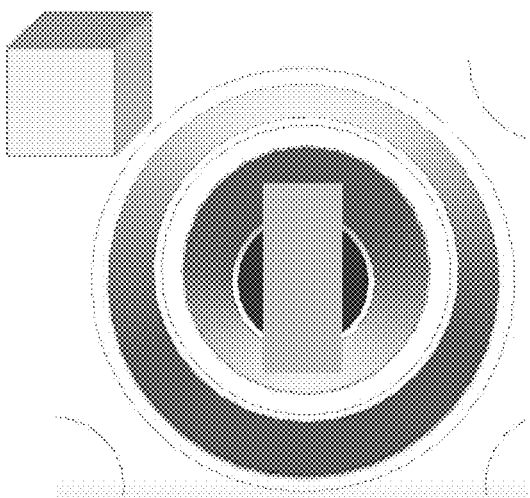
Figure 2C:
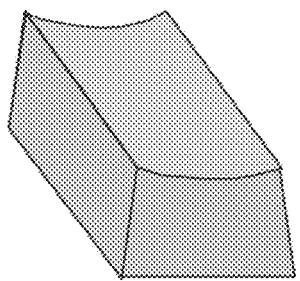

FIG. 2 shows an exemplary design of a reservoir from a device having particles and having a raised platform on the bottom of the reservoir. The raised platform contains a depression on the top surface of the platform, which catches settling particles, and reduces the amount of particles that settle onto the bottom surface of the reservoir. FIGS. 2A and 2B show the side and top schematic views of the example reservoir design, respectively. FIG. 2C shows a drawing of an exemplary platform.

Example 2

Figure 3A:
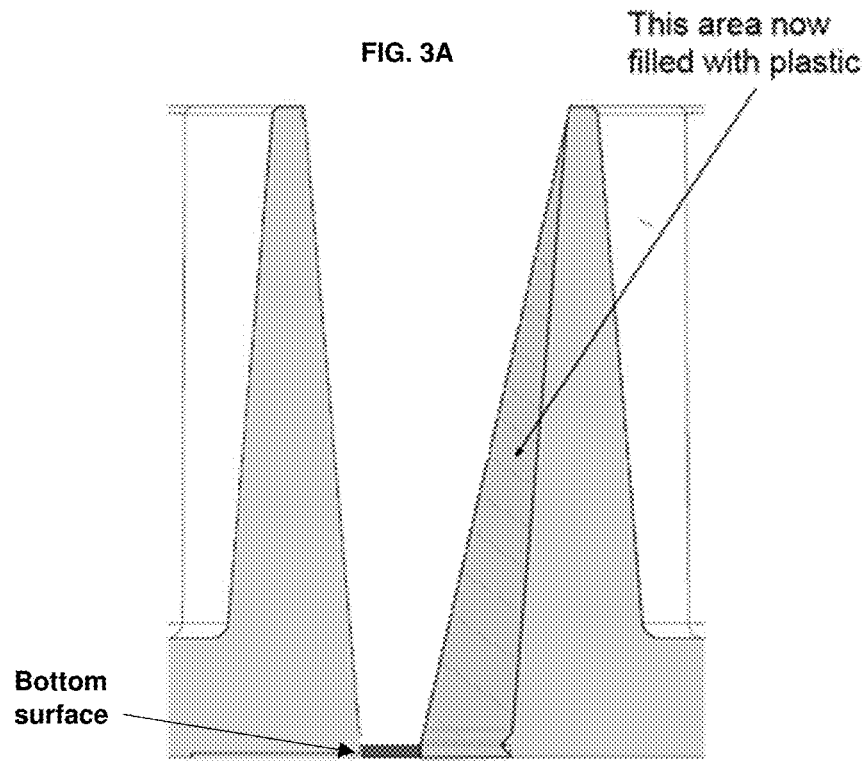
FIGS. 3A-3C show an exemplary design of a reservoir with reduced surface area on the bottom surface.
Figure 3B:
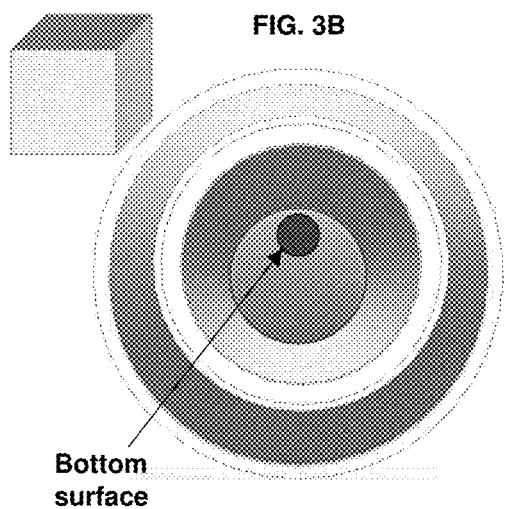
Figure 3C:
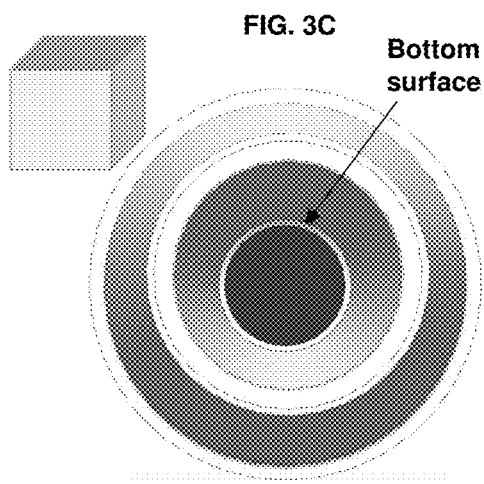

FIGS. 3A-3C show an exemplary design of a reservoir shaped to reduce the surface area of the bottom surface. FIGS. 3B and 3C show the top view of a reservoir with (FIG. 3B) and without (FIG. 3C) the reduction in bottom surface area.

Example 3

Figure 4A:
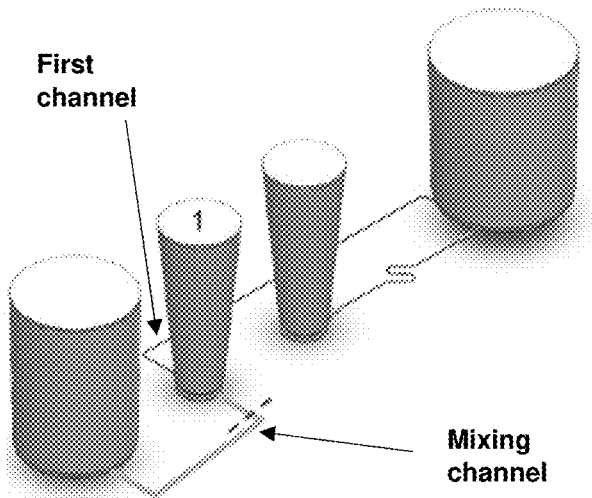
FIGS. 4A-4B show an exemplary design of a reservoir fluidically disposed between a first channel and a mixing channel.
Figure 4B:
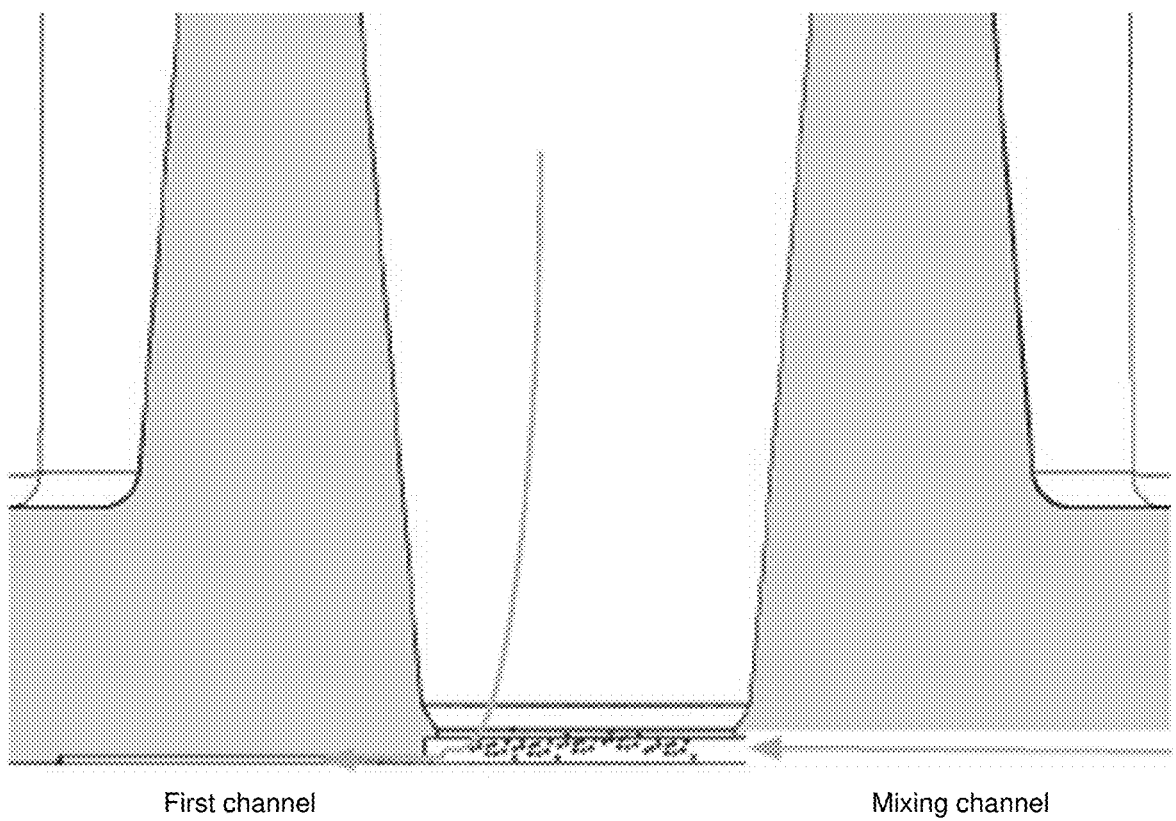

FIGS. 4A-4B show an exemplary design of a reservoir and fluidically connected channels and additional reservoirs from a device including a reservoir fluidically disposed between a first channel and a mixing channel. The first channel and reservoir contain a first liquid containing biological particles, and the mixing channel contains a secondary liquid which may be substantially the same as the first liquid. Flowing the secondary liquid from the mixing channel into the reservoir resuspends the particles that settle onto the bottom surface of the reservoir.

Example 4

Figure 5A:
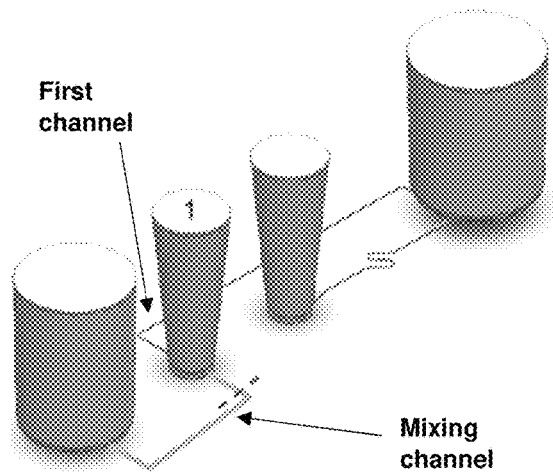
FIGS. 5A-5B show an exemplary design of a reservoir fluidically disposed between a first channel and a mixing channel.
Figure 5B:
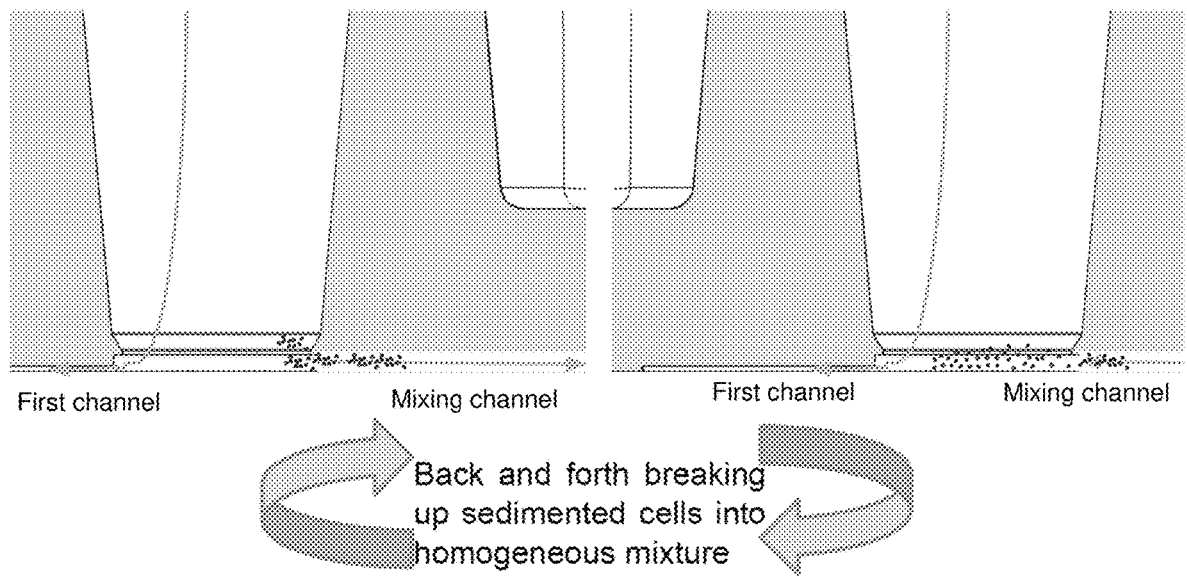

FIGS. 5A-5B show an exemplary design of a reservoir and fluidically connected channels and additional reservoirs from a device including a reservoir fluidically disposed between a first channel and a mixing channel. The first channel and reservoir contain a first liquid containing biological particles. As biological particles settle onto the bottom surface of the reservoir during droplet production, the first liquid can be flowed from the reservoir into the mixing channel and from the mixing channel back out into the reservoir to resuspend settled particles.

Other embodiments are in the claims.

What is claimed is:

1. A device for producing droplets comprising:
   (a) a first channel having a first height, a first width, a first proximal end, and a first distal end;
   (b) a reservoir having a reservoir height greater than the first height, and an outlet in fluid communication with the first proximal end;
   (c) a platform having a platform height less than the reservoir height and comprising a depression on a top surface, wherein the platform is disposed in the reservoir; and
   (d) a droplet source region in fluid communication with the first distal end.

2. The device of claim 1, wherein the platform height is less than 90% of the reservoir height.

3. The device of claim 2, wherein the platform height is between about 300 µm and about 9.9 mm.

4. The device of claim 3, wherein the platform height is about 700 µm.

5. The device of claim 1, wherein a side of the platform is slanted.

6. The device of claim 1, wherein the depression is curved.

7. The device of claim 1, wherein the depression has a depth of at least 50 µm.

8. The device of claim 1, further comprising a second channel having a second height, a second width, a second proximal end, and a second distal end, wherein the second channel intersects the first channel between the first proximal end and the first distal end.

9. The device of claim 1, wherein the droplet source region comprises a shelf region having a third height and a third width greater than the first width and being in fluid communication with the first distal end; and a step region comprising a wall having a fourth height greater than the first and third heights, wherein the shelf region is disposed between the step region and the first distal end.

10. A method for producing droplets comprising:
   (a) providing a device of claim 1; and
   (b) flowing a first liquid comprising particles from the reservoir to the droplet source region via the first channel to produce droplets of the first liquid in a second liquid, wherein particles settle from the first liquid in the reservoir into the depression.

11. The method of claim 10, wherein, when the first liquid is depleted from the reservoir, the settled particles remain in the depression.

12. The method of claim 10, wherein step (b) produces droplets comprising one of the particles.

13. The method of claim 10, wherein the particles are cells or particulate components thereof.

14. The method of claim 10, wherein the device further comprises a second channel having a second height, a second width, a second proximal end, and a second distal end, wherein the second channel intersects the first channel between the first proximal end and the first distal end, and step (b) further comprises flowing a third liquid in the second channel to the intersection to combine the first and third liquids, wherein the droplets comprise the combined first and third liquids.

15. The method of claim 14, wherein the third liquid comprises second particles, and step (b) produces droplets comprising one of the particles and one of the second particles.

16. The method of claim 10, wherein the droplet source region comprises a shelf region having a third height and a third width greater than the first width and being in fluid communication with the first distal end; and a step region comprising a wall having a fourth height greater than the first and third heights, wherein the shelf region is disposed between the step region and the first distal end.

17. A device for producing droplets comprising:
   (a) a first channel having a first height, a first width, a first proximal end, and a first distal end;
   (b) a reservoir having a reservoir height greater than the first height and an outlet in fluid communication with the first proximal end, wherein the reservoir comprises a slanted wall that asymmetrically reduces the cross-sectional area of the reservoir adjacent to the outlet by between 75-90%, wherein the cross-sectional area of the reservoir adjacent to the outlet does not overlap with the radial axis of symmetry of the cross-sectional area of the reservoir at the reservoir height; and
   (c) a droplet source region.

18. The device of claim 17, further comprising a second channel having a second height, a second width, a second proximal end, and a second distal end, wherein the second channel intersects the first channel between the first proximal end and the first distal end.

19. A device for producing droplets comprising:
   (a) a first channel having a first height, a first width, a first proximal end, and a first distal end;
   (b) a reservoir having a reservoir height greater than the first height and an outlet in fluid communication with the first proximal end, wherein the reservoir comprises a slanted wall that reduces the cross-sectional area of the reservoir adjacent to the outlet by between 75-90%; and
   (c) a droplet source region, wherein the droplet source region comprises a shelf region having a third height and a third width greater than the first width and being in fluid communication with the first distal end; and a step region comprising a wall having a fourth height greater than the first and third heights, wherein the shelf region is disposed between the step region and the first distal end.

20. A method of producing droplets comprising:
   (a) providing a device of claim 19; and
   (b) flowing a first liquid comprising particles from the reservoir to the droplet source region via the first channel to produce droplets of the first liquid in a second liquid, wherein particles settling from the first liquid in the reservoir flow through the outlet.

21. The method of claim 20, wherein step (b) produces droplets comprising one of the particles.

22. The method of claim 21, wherein the particles are cells or particulate components thereof.

23. The method of claim 20, wherein the device further comprises a second channel having a second height, a second width, a second proximal end, and a second distal end, wherein the second channel intersects the first channel between the first proximal end and the first distal end, and step (b) further comprises flowing a third liquid in the second channel to the intersection to combine the first and third liquids, wherein the droplets comprise the combined first and third liquids.

24. The method of claim 23, wherein the third liquid comprises second particles, and step (b) produces droplets comprising one of the particles and one of the second particles.

* * * * *